US008530501B2

(12) United States Patent
Pandey et al.

(10) Patent No.: US 8,530,501 B2
(45) Date of Patent: Sep. 10, 2013

(54) SALTS AND CRYSTALLINE FORMS OF A FACTOR XA INHIBITOR

(75) Inventors: Anjali Pandey, Fremont, CA (US); Louisa Jane Quegan, Impington (GB)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 237 days.

(21) Appl. No.: 12/970,785

(22) Filed: Dec. 16, 2010

(65) Prior Publication Data

US 2011/0178135 A1 Jul. 21, 2011

Related U.S. Application Data

(60) Provisional application No. 61/287,683, filed on Dec. 17, 2009.

(51) Int. Cl.
*A61K 31/4439* (2006.01)
*A61K 31/4436* (2006.01)
*C07D 409/14* (2006.01)

(52) U.S. Cl.
USPC .................................. 514/341; 546/275.1

(58) Field of Classification Search
USPC ........................ 546/275.1; 514/341
See application file for complete search history.

(56) References Cited

U.S. PATENT DOCUMENTS

| | | | |
|---|---|---|---|
| 6,376,515 B2 | 4/2002 | Zhu et al. | |
| 6,423,713 B1 | 7/2002 | Anantanarayan et al. | |
| 6,627,646 B2 * | 9/2003 | Bakale et al. | 514/322 |
| 6,835,739 B2 | 12/2004 | Zhu et al. | |
| 6,844,367 B1 | 1/2005 | Zhu et al. | |
| 6,906,063 B2 | 6/2005 | Scarborough et al. | |
| 7,022,695 B2 | 4/2006 | Zhu et al. | |
| 7,157,456 B2 | 1/2007 | Straub et al. | |
| 7,285,565 B2 | 10/2007 | Zhu et al. | |
| 7,312,235 B2 | 12/2007 | Zhu et al. | |
| 7,314,874 B2 | 1/2008 | Zhu et al. | |
| 7,342,013 B2 | 3/2008 | Zhu et al. | |
| 7,521,470 B2 | 4/2009 | Zhu et al. | |
| 7,598,276 B2 | 10/2009 | Grant et al. | |
| 7,696,352 B2 | 4/2010 | Zhu et al. | |
| 7,727,981 B2 | 6/2010 | Zhu et al. | |
| 7,727,982 B2 | 6/2010 | Zhu et al. | |
| 7,763,608 B2 | 7/2010 | Song et al. | |
| 7,767,697 B2 | 8/2010 | Song et al. | |
| 8,063,036 B2 | 11/2011 | Zhu et al. | |
| 8,063,077 B2 | 11/2011 | Song et al. | |
| 2003/0153610 A1 | 8/2003 | Straub et al. | |
| 2003/0162690 A1 | 8/2003 | Zhu et al. | |
| 2005/0171358 A1 | 8/2005 | Shimozono et al. | |
| 2006/0100193 A1 | 5/2006 | Zhu et al. | |
| 2007/0043079 A1 | 2/2007 | Habashita et al. | |
| 2007/0066615 A1 | 3/2007 | Gerdes et al. | |
| 2007/0112039 A1 | 5/2007 | Grant et al. | |
| 2007/0185092 A1 | 8/2007 | Zhu et al. | |
| 2007/0259924 A1 | 11/2007 | Song et al. | |
| 2008/0051578 A1 | 2/2008 | Dahmann et al. | |
| 2008/0153876 A1 | 6/2008 | Sinha et al. | |
| 2008/0241233 A1 | 10/2008 | Sims et al. | |
| 2008/0254036 A1 | 10/2008 | Sinha et al. | |
| 2008/0279845 A1 | 11/2008 | Conley et al. | |
| 2008/0293704 A1 | 11/2008 | Jia et al. | |
| 2009/0098119 A1 | 4/2009 | Lu et al. | |
| 2009/0186810 A1 | 7/2009 | Zwaal et al. | |
| 2009/0298806 A1 | 12/2009 | Zhu et al. | |
| 2010/0063113 A1 | 3/2010 | Grant et al. | |
| 2010/0125052 A1 | 5/2010 | Lu et al. | |
| 2010/0197929 A1 | 8/2010 | Scarborough et al. | |
| 2010/0234352 A1 | 9/2010 | Zhu et al. | |
| 2010/0255000 A1 | 10/2010 | Sinha et al. | |
| 2011/0015128 A1 | 1/2011 | Sinha et al. | |
| 2012/0178733 A1 | 7/2012 | Zhu et al. | |

FOREIGN PATENT DOCUMENTS

| | | |
|---|---|---|
| CA | 2 453 846 | 1/2003 |
| CA | 2 653 666 | 12/2007 |
| DE | 10322469 | 12/2004 |
| JP | 2000-178243 | 6/2000 |
| JP | 2003-519141 | 6/2003 |
| WO | WO 99/07379 | 2/1999 |
| WO | WO 99/28317 | 6/1999 |
| WO | WO 01/19788 | 3/2001 |
| WO | WO 01/21160 | 3/2001 |
| WO | WO 01/47919 | 7/2001 |
| WO | WO 01/64642 | 9/2001 |
| WO | WO 01/64643 | 9/2001 |
| WO | WO 01/91558 | 12/2001 |
| WO | WO 02/00651 | 1/2002 |
| WO | WO 02/079145 | 10/2002 |
| WO | WO 03/000256 | 1/2003 |
| WO | WO 03/008395 | 1/2003 |
| WO | WO 03/059894 | 7/2003 |
| WO | WO 2004/092136 | 10/2004 |
| WO | WO 2004/101531 | 11/2004 |

(Continued)

OTHER PUBLICATIONS

U.S. Pharmacopia #23, National Formulary #18, 1995, 1843-1844.*
Concise Encyclopedia Chemistry, NY: Walter de Gruyter, 1993, 872-873.*
Muzaffar et al., "Polymorphism and Drug Availability, etc.," J of Pharm. (Lahore), 1979, 1(1), 59-66.*
Doelker, english translation of Ann. Pharm. Fr., 2002, 60: 161-176, pp. 1-39.*
Doelker, english translation of S.T.P, Pratiques (1999), 9(5), 399-409, pp. 1-33.*
Singhal et al., "Drug Polymorphism, etc.," Advanced Drug Delivery reviews 56, p. 335-347 (2004).*
CMU Pharmaceutical polymorphism, internet, p. 1-3 (2002) (print out Apr. 3, 2008).*
Otuska et al., "Effect of Polymorphic, etc.," Chem. Pharm. Bull., 47(6) 852-856 (1999).*
Taday et al., "Using Terahertz, etc.," J of Pharm. Sci., 92(4), 2003, 831-838.*
International Search Report for PCT/US2010/060885, dated Jul. 14, 2011, 5 pages.
US 7,479,487, 01/2009, Zhu et al. (withdrawn).
Banker, G.S. et al, "Modern Pharmaceutics, 3$^{rd}$ ed.", Marcel Dekker, New York, 1996, pp. 451 and 596.
In the Pipeline, online, accessed Jun. 16, 2008, "http://pipeline.corante.com/archives/2006/01/24/the_examiner_finally_snaps.php".
Daniel Dube and Andrew A. Scholte, Reductive-N-Alkylation of Amides, Carbamates, and Ureas, Tetrahedron Letters, 1999, vol. 40, 2295-2298.

(Continued)

*Primary Examiner* — Patricia L Morris
(74) *Attorney, Agent, or Firm* — Foley & Lardner LLP

(57) ABSTRACT

The present invention provides salts and crystalline forms of the compound 5-chloro-N-((1-(4-(2-oxopyridin-1(2H)-yl)phenyl)-1H-imidazol-4-yl)methyl)thiophene-2-carboxamide, and pharmaceutical compositions and method of use thereof.

8 Claims, 27 Drawing Sheets

(56) References Cited

FOREIGN PATENT DOCUMENTS

| WO | WO 2004/101557 | 11/2004 |
|----|----|----|
| WO | WO 2004/106329 | 12/2004 |
| WO | WO 2005/032468 | 4/2005 |
| WO | WO 2005/034867 | 4/2005 |
| WO | WO 2005/035528 | 4/2005 |
| WO | WO 2005/082892 | 9/2005 |
| WO | WO 2006/002099 | 1/2006 |
| WO | WO 2007/007588 | 1/2007 |
| WO | WO 2007/025940 | 3/2007 |
| WO | WO 2007/056219 | 5/2007 |
| WO | WO 2007/112367 | 10/2007 |
| WO | WO 2007/131179 | 11/2007 |
| WO | WO 2007/137791 | 12/2007 |
| WO | WO 2008/057972 | 5/2008 |
| WO | WO 2008/073670 | 6/2008 |
| WO | WO 2008/086188 | 7/2008 |
| WO | WO 2008/086226 | 7/2008 |
| WO | WO 2008/121721 | 10/2008 |
| WO | WO 2008/127682 | 10/2008 |
| WO | WO 2008/137787 | 11/2008 |
| WO | WO 2009/042962 | 4/2009 |
| WO | WO 2010/056765 | 5/2010 |
| WO | WO/2010/117729 | 10/2010 |
| WO | WO/2011/008885 | 1/2011 |

OTHER PUBLICATIONS

Ostrovsky et al., "Analysis of Activity for Factory Xa Inhibitors Based on Monte Carlo Simulations", *J. Med. Chem.*, 46, 5691-5699 (2003).

Roehrig et al., "Discovery of the Novel Antithrombotic Agent 5-Chloro-N-(((5S)-2-oxo-3[4-(3-oxomorpholin-4-yl)phenyl]-1,3-oxazol idin-5-yl)methyl)thiophene 2-carboxamide (BAY 59/7939): An Oral, Direct Factor Xa Inhibitor", *J. Med. Chem.*, 48, 5900-5908 (2005).

Qiao et al. "SAR and X-ray structures of enantiopure 1,2-cis-(1R,2S)-cyclopentyldiamine and cyclohexyldiamine derivatives as inhibitors of coagulation Factor Xa" Bioorganic & Medicinal Chemistry Letters 2007, 17, 4419-4427.

Shi et al. "Cyanoguanidine-based lactam derivatives as a novel class of orally bioavailable factor Xa inhibitors" Bioorganic & Medicinal Chemistry Letters 19 (2009) 4034-4041.

Smallheer et al. "Sulfonamidolactam inhibitors of coagulation factor Xa" Bioorganic & Medicinal Chemistry Letters 2008, 18, 2428-2433.

Song et al. "Substituted Acrylamides as Factor Xa Inhibitors: Improving Bioavailability by PI Modification" Bioorganic & Medicinal Chemistry Letters 12 (2002) 2043-2046.

Wolff, Manfred E. "Burger's Medicinal Chemistry, 5$^{th}$ ed, Part I", John Wiley & Sons, 1995, pp. 975-977.

\* cited by examiner

SALTS AND CRYSTALLINE FORMS OF A FACTOR XA INHIBITOR

CROSS REFERENCE TO RELATED APPLICATIONS

This application claims the benefit under 35 U.S.C. §119 (e) of U.S. Provisional Application Ser. No. 61/287,683 filed on Dec. 17, 2009, which is hereby incorporated by reference in its entirety.

BACKGROUND OF THE INVENTION

1. Field of the Invention

This invention is directed to salts of a factor Xa inhibitor 5-chloro-N-((1-(4-(2-oxopyridin-1(2H)-yl)phenyl)-1H-imidazol-4-yl)methyl)thiophene-2-carboxamide, crystalline forms of the factor Xa inhibitor and compositions and methods thereof.

2. State of the Art 5-chloro-N-((1-(4-(2-oxopyridin-1(2H)-yl)phenyl)-1H-imidazol-4-yl)methyl)thiophene-2-carboxamide, having the formula of:

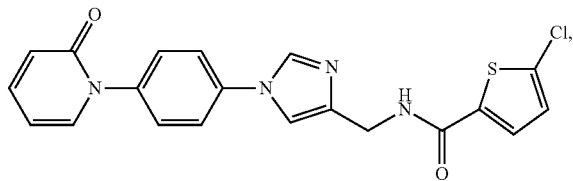 [SMILES: O=C(NCc1cn(-c2ccc(-n3ccccc3=O)cc2)cn1)c1ccc(Cl)s1]

(collectively referred to as "Compound I" herein), is a factor Xa inhibitor described in U.S. Pat. Nos. 7,763,608 and 7,767,697 (which are incorporated by reference in their entirety) and has been shown to have anticoagulation activity in vivo.

SUMMARY OF THE INVENTION

In one aspect, this invention provides a crystalline Form A of the mesylate salt of 5-chloro-N-((1-(4-(2-oxopyridin-1(2H)-yl)phenyl)-1H-imidazol-4-yl)methyl)thiophene-2-carboxamide, having the formula of:

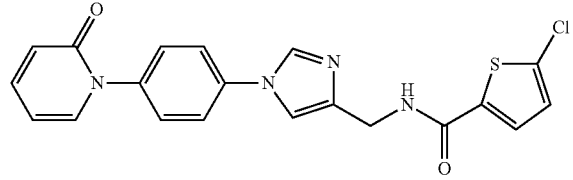 [SMILES: O=C(NCc1cn(-c2ccc(-n3ccccc3=O)cc2)cn1)c1ccc(Cl)s1]

(also referred to as Compound I), which crystalline form is characterized by an X-ray powder diffraction pattern having at least six 2θ° peaks selected from the group consisting of: about 18.05, about 20.30, about 20.95, about 21.85, about 23.20, about 26.13, and about 26.85.

In one aspect, this invention provides the mesylate salt of Compound I wherein at least a portion of the salt is present in the crystalline Form A.

In one aspect, this invention provides a method for preparing the crystalline Form A of the mesylate salt of Compound I comprising combining the free base of Compound I with at least one equivalent of methanesulfonic acid in a solvent comprising methylethyl ketone, and optionally tetrahydrofuran.

In one aspect, this invention provides a crystalline Form B of a mesylate salt of 5-chloro-N-((1-(4-(2-oxopyridin-1(2H)-yl)phenyl)-1H-imidazol-4-yl)methyl)thiophene-2-carboxamide, having the formula of:

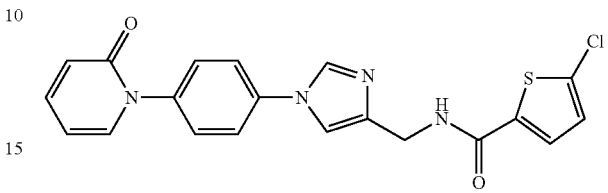

(also referred to as Compound I), which crystalline form is characterized by an X-ray powder diffraction pattern having at least six 2θ° peaks selected from the group consisting of: about 16.96, about 18.95, about 20.41, about 21.34, about 21.85, about 22.75, about 25.75 and about 26.65.

In another aspect, this invention provides a phosphate salt of Compound I, wherein at least a portion of the salt is present in a crystalline Form B.

In one aspect, this invention provides a method for preparing the crystalline Form B of the mesylate salt of Compound I comprising recrystallizing a mesylate salt of Compound I in a solvent comprising acetone and optionally water and/or methylethyl ketone.

In another aspect, this invention provides a 1-hydroxy-2-naphthoate salt of Compound I. In some embodiments, at least a portion of the 1-hydroxy-2-naphthoate salt is present in a crystalline form. In some embodiments, this invention provides a crystalline form of the 1-hydroxy-2-naphthoate salt of Compound I.

In another aspect, this invention provides a crystalline form of a phosphate salt of Compound I. In some embodiments, the crystalline form of the phosphate salt of Compound I is selected from the group consisting of a crystalline form having an X-ray powder diffraction pattern substantially the same as (1) an X-ray powder diffraction pattern having at least four 2θ° peaks selected from the group consisting of about 6.5, about 8.0, about 8.8, about 11.0, about 14.5, about 17.3, and about 18.2; or (2) an X-ray powder diffraction pattern having at least four 2θ° peaks selected from the group consisting of about 4, about 6.5, about 8.2, about 13.9, about 14.5, about 16, about 17.45, about 18.2, about 19.15, about 20.1, about 21.45, about 22.35, about 23.5, about 24.0, about 25.2, about 27.65, and about 28.25.

In some embodiments, at least a portion of the phosphate salt is present in a crystalline form.

In another aspect, this invention provides a pharmaceutical composition comprising the salt of Compound I.

In another aspect, this invention provides a method for preventing or treating a condition in a mammal characterized by undesired thrombosis comprising administering to said mammal a therapeutically effective amount of the salt of Compound I as described herein.

This and other embodiments will be further described in the text that follows.

BRIEF DESCRIPTION OF THE DRAWINGS

in FIG. 8a is likely due to re-crystallization after the monohydrate crystalline melted.

DETAILED DESCRIPTION OF THE INVENTION

Figure 1:
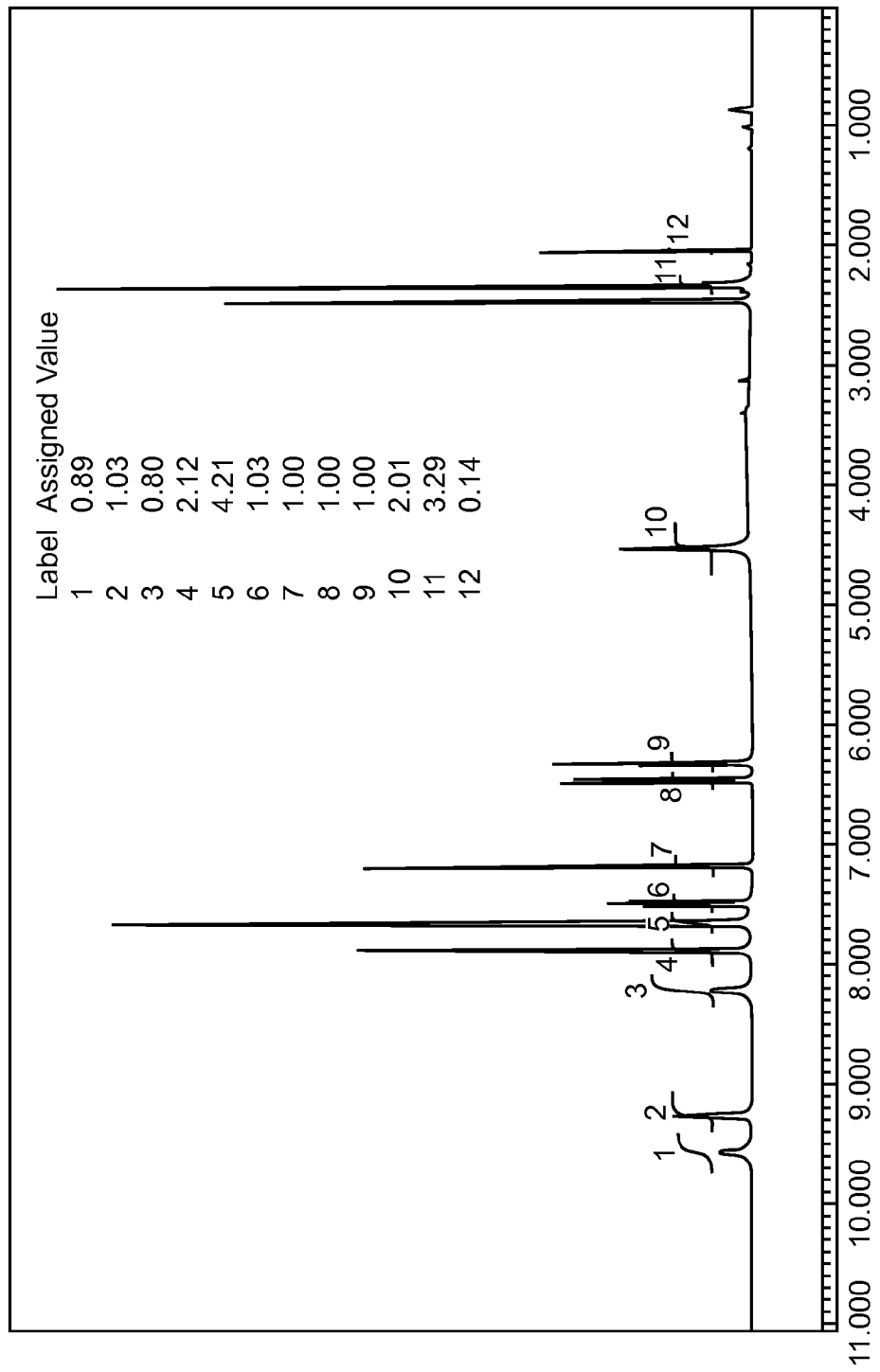
FIG. 1 provides a nuclear magnetic resonance spectrum of a mesylate salt of Compound I.
Figure 2:
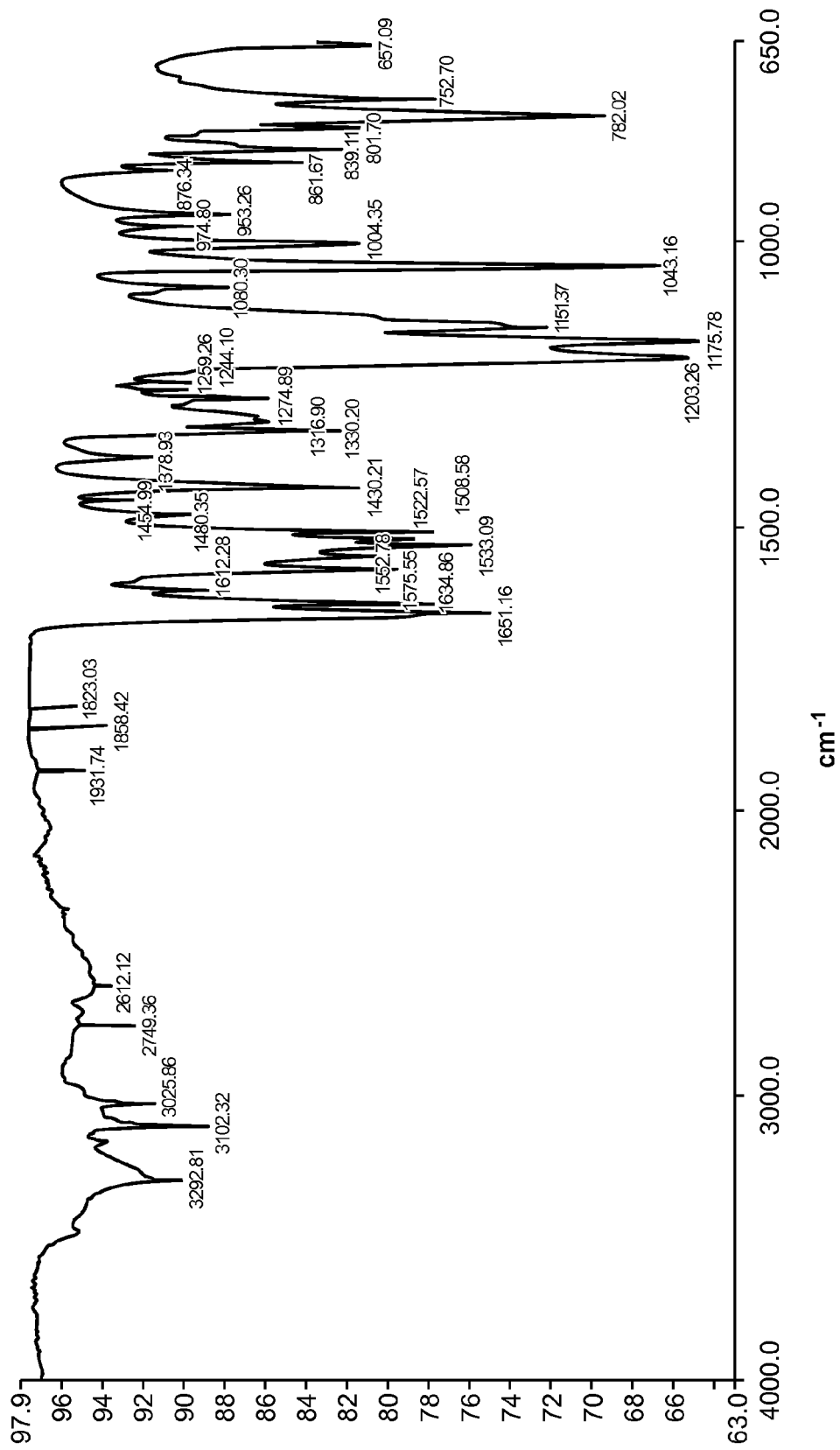
FIG. 2 provides an infrared spectrum of the mesylate salt of Compound I.

As used herein, the following definitions shall apply unless otherwise indicated.

DEFINITIONS

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The term 5-chloro-N-((1-(4-(2-oxopyridin-1(2H)-yl)phenyl)-1H-imidazol-4-yl)methyl)thiophene-2-carboxamide" refers to the compound of the structure:

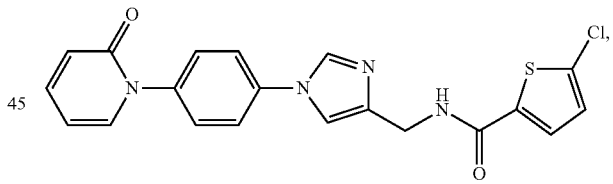

which is also referred to as "Compound I." This compound is described in U.S. Pat. Nos. 7,763,608 and 7,767,697.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles. For example, the proton of a salt of Compound I may be in different positions of a imidazole ring the molecule. A salt of Compound I includes all structural variations due to the position of the salt proton unless otherwise indicated.

"Patient" refers to mammals and includes humans and non-human mammals.

"Amorphous" refers to a composition comprising a compound that contains no or too little crystalline content of the compound to yield a discernable pattern by XRPD or other diffraction techniques. For example, glassy materials are a type of amorphous material. Amorphous materials do not have a true crystal lattice, and are glassy, technically resembling very viscous non-crystalline liquids. Glasses may better be described as quasi-solid amorphous material. As is known in the art, an amorphous material refers to a quasi-solid. A compound in an amorphous state may be produced by rapidly evaporating solvent from a solution of a compound, or by grinding, pulverizing or otherwise physically pressurizing or abrading the compound while in a crystalline state.

"Crystalline" refers to a material that contains a specific compound or a salt of the compound, which may be hydrated and/or solvated, and has sufficient crystalline content to exhibit a discernable diffraction pattern by XRPD or other diffraction techniques. Crystallines can be characterized by their crystalline structure (X-ray diffraction pattern), their thermal properties (as determined by DSC and TGA), stability, solubility, etc. The X-ray diffraction pattern is presented as characteristic 2θ° peaks and one skilled in the art can readily identify a crystalline form of a compound or salt based on the characteristic 2θ° peaks of an X-ray diffraction pattern of the polymorph. When two X-ray diffraction patterns have at least 4, preferably at least 6, 8, or 10 2θ° peaks, or more preferably all peaks, that do not vary more than ±0.2, ±0.1, ±0.05 or ±0.02 degrees, it is deemed that the X-ray diffraction patterns are substantially the same. In some embodiments, characteristic peaks are those having a relative intensity of 25% or more. In some embodiments, characteristic peaks are those that have a relative intensity of 10% or more. In some embodiments, characteristic peaks are those that have a relative intensity of 5% or more.

A crystalline of a compound or a salt may be characterized by properties including one or more of the following as described in details herein:
    its X-ray powder diffraction pattern (XRPD);
    its infrared spectrum (IR);
    its differential scanning calorimetry (DSC);
    its thermogravimetric analysis (TGA);
    its vapor sorption curve, such as Gravimetric Vapour Sorption (GVS), and
    crystal structure, such as unit cell structure.

In some cases, a crystalline material that is obtained by direct crystallization of a compound dissolved in a solvent or solvent mixture or solution or interconversion of crystals obtained under different crystallization conditions, may have crystals that contain the solvent used in the crystallization. Such compositions may be referred to as a crystalline solvate. When the solvent is water, such compositions may be referred to as a crystalline hydrate. Also, the specific solvent system and physical embodiment in which the crystallization is performed, collectively termed as crystallization conditions, may result in the crystalline material having physical and chemical properties that are unique to the crystallization conditions. This may be due to the orientation of the chemical moieties of the compound with respect to each other within the crystal and/or the predominance of a specific polymorphic or pseudopolymorphic form of the compound in the crystalline material. General methods for precipitating and crystallizing a compound may be applied to prepare the various polymorphs or pseudopolymorphs described herein. These general methods are known to one skilled in the art of synthetic organic chemistry and pharmaceutical formulation, and are described, for example, by J. March, "Advanced Organic Chemistry: Reactions, Mechanisms and Structure," 4th Ed. (New York: Wiley-InterScience, 1992) and *Remington: The Science and Practice of Pharmacy*, A. Gennaro, ed., 21st edition,-Lippincott, Williams & Wilkins, Philadelphia, Pa., 2006.

"Polymorph" or "polymorphic form" refers to a crystalline form of a substance that is distinct from another crystalline form but that shares the same chemical formula. The different polymorphic forms of the same compound can have an impact on one or more physical properties, such as stability, solubility, melting point, bulk density, flow properties, bioavailability, etc.

"Pseudopolymorph" refers to a crystalline form of a hydrate or solvate of a compound. In contrast to polymorphs, pseudopolymorphs are chemically identical except differ in the amount of water or solvent bound in the crystal lattice. Depending on the solvent used during synthesis and/or crystallization some compounds form hydrates (with water) or solvates (with other solvents) in different stoichiometric ratio. Pseudopolymorphs may show different physical properties like habitus, stability, dissolution rate and bioavailability as known for polymorphs.

It is to be understood that when a value is recited for a condition or a yield, the value may vary within a reasonable range, such as ±5%, ±1%, and ±0.2%. Similarly, the term "about" when used before a numerical value indicates that the value may vary within reasonable range, such as ±5%, ±1%, and ±0.2%. When "about" is used before a 2θ° peak of an XRPD, it indicates that the 2θ° value may vary±0.2, ±0.1, ±0.05, or ±0.02 degrees.

"Treatment" or "treating" means any treatment of a disease or disorder in a subject, including:
    preventing or protecting against the disease or disorder, that is, causing the clinical symptoms not to develop;
    inhibiting the disease or disorder, that is, arresting or suppressing the development of clinical symptoms; and/or
    relieving the disease or disorder that is, causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

"Therapeutically effective amount" refers to that amount of a compound of this invention that is sufficient to effect treatment, as defined below, when administered to a subject in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

"Disease condition" refers to a disease state for which the compounds, compositions and methods of the present invention are being used against.

"Blood sample" refers to whole blood taken from a subject, or any fractions of blood including plasma or serum.

Salts, Polymorphs and Pseudopolymorphs

In one aspect, this invention provides salts, polymorphs and pseudopolymorphs of Compound I. Several salt forms of Compound I were formed, which include a mesylate salt, phosphate salt, thiocyanate salt and 1-hydroxy-2-naphthoate salt. However, Compound I was unable to form salts under tested conditions with certain acids, such as glutamic acid and aspartic acid. While not intended to be bound by any theory, it is contemplated that this may be due to the poor solubility of the free base of Compound I. Further, the thiocyanate salt was not reproduced upon scaling up.

In one embodiment, this invention provides a mesylate salt of Compound I. The mesylate salt may exist in an amorphous form or in a crystalline form or a mixture of an amorphous form and a crystalline form or a mixture of several polymorphic and/or pseudopolymorphic forms. In some embodiments, at least a portion of the salt is in a crystalline form.

"The mesylate salt of Compound I" refers to the salt formed between Compound I and methanesulfonic acid ($CH_3SO_3H$), in an equivalent ratio of, for example, about 1 to 1.

In some embodiments, the mesylate salt of Compound I is of the formula:

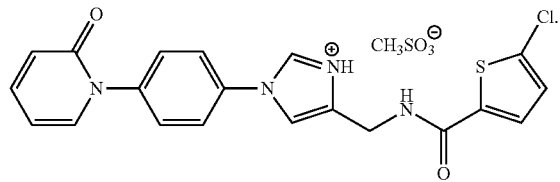 [SMILES: O=C(NCc1cn(-c2ccc(-n3ccccc3=O)cc2)c[nH+]1)c1ccc(Cl)s1 ; "CH3SO3"]

In some embodiments, provided is a crystalline Form A or Form B of the mesylate salt of Compound I. A crystalline polymorph of a given compound is chemically identical to any other crystalline polymorph of that compound in containing the same atoms bonded to one another in the same way, but differs in its crystal forms. Pseudopolymorphs are chemically identical except differ in the amount of water or solvent bound in the crystal lattice. Depending on the solvent used during synthesis and/or crystallization some compounds form hydrates (with water) or solvates (with other solvents) in different stoichiometric ratio. The different crystalline forms of the same compound can have an impact on one or more physical properties, such as stability, solubility, melting point, bulk density, flow properties, bioavailability, etc.

Form A and Form B, of the mesylate salt of Compound I provide good stability, solubility, melting point, bulk density, and flow properties. Crystalline Form A has an excellent physical and chemical stability and has a higher melting point than Form B. U.S. Provisional Patent Application No. 61/287, 681, filed on Dec. 17, 2009, and U.S. patent application Ser. No. 12/970,818, filed on Dec. 16, 2010, both of which are titled "Crystalline Forms of a Factor Xa Inhibitor" and incorporated herein by reference in their entirety, describe additional crystalline forms C, D, and E of the mesylate salt of Compound I, which are desirable for other reasons. Among these crystalline forms, Form A has the highest melting point which might provide better stability during formulation of compositions suitable for pharmaceutical use.

Figure 3A:
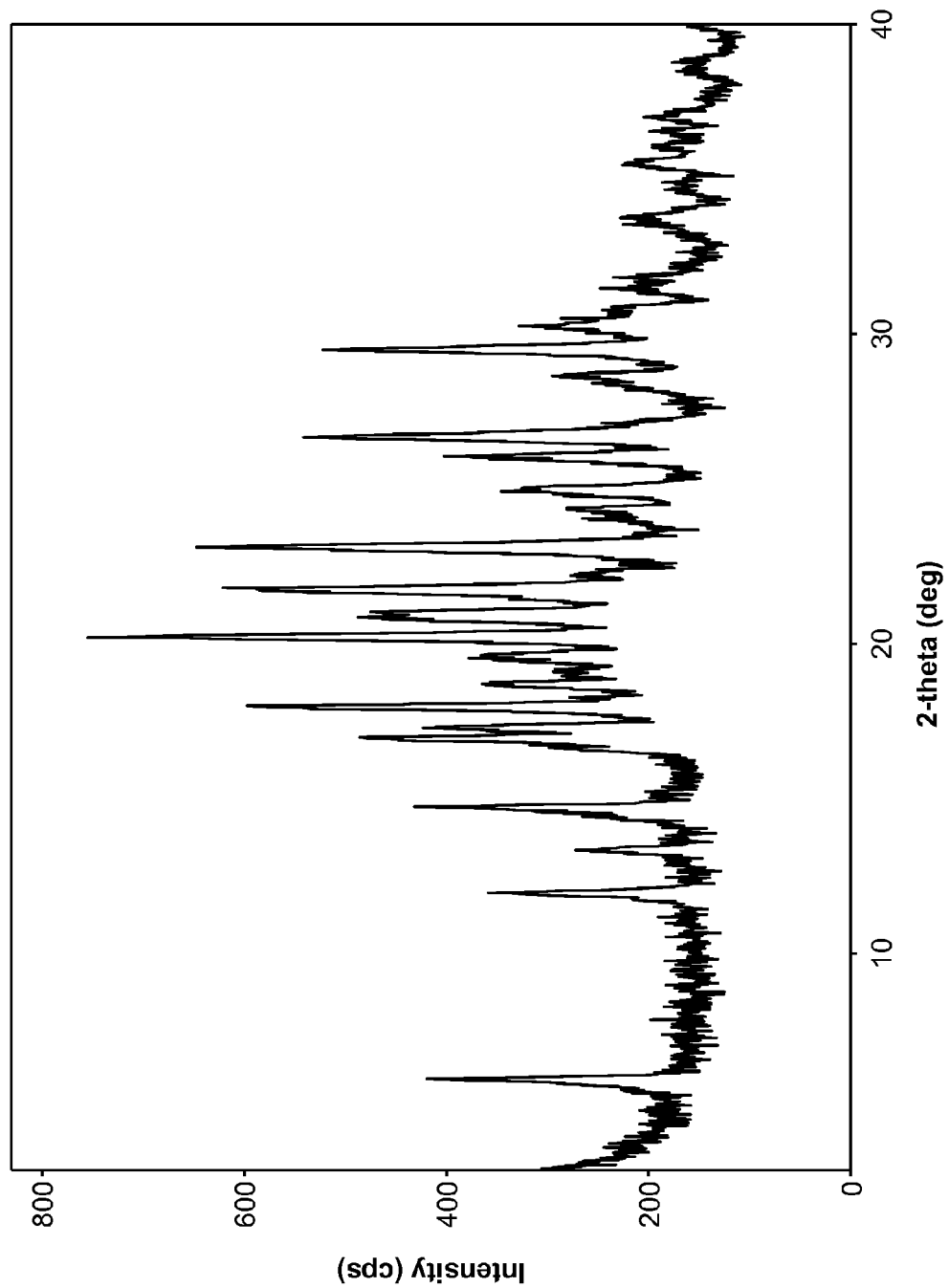
FIGS. 3a and 3b provides X-ray powder diffraction (XRPD) patterns of crystalline Form A of the mesylate salt of Compound I.
Figure 3B:
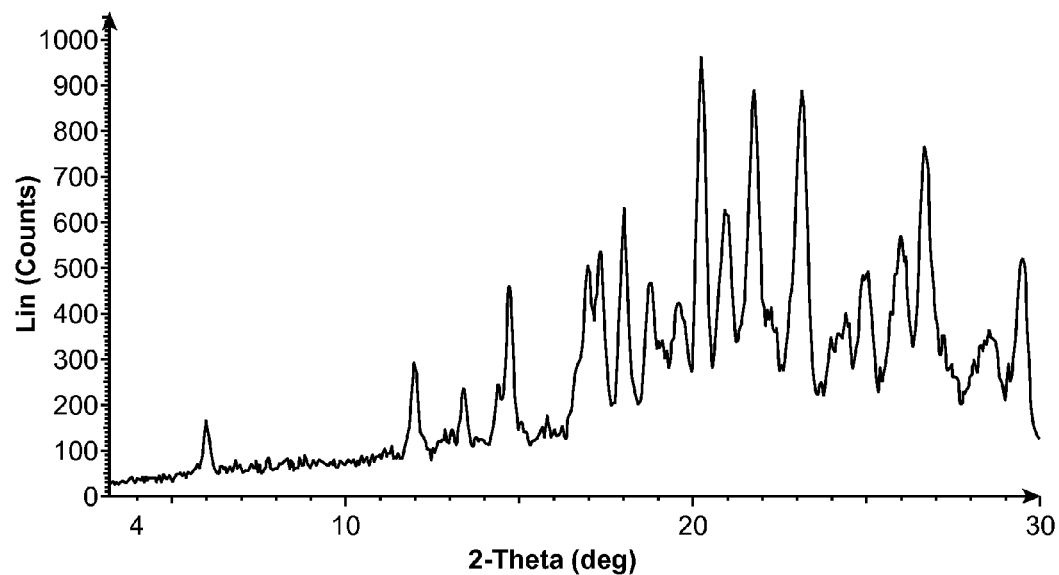
Figure 28:
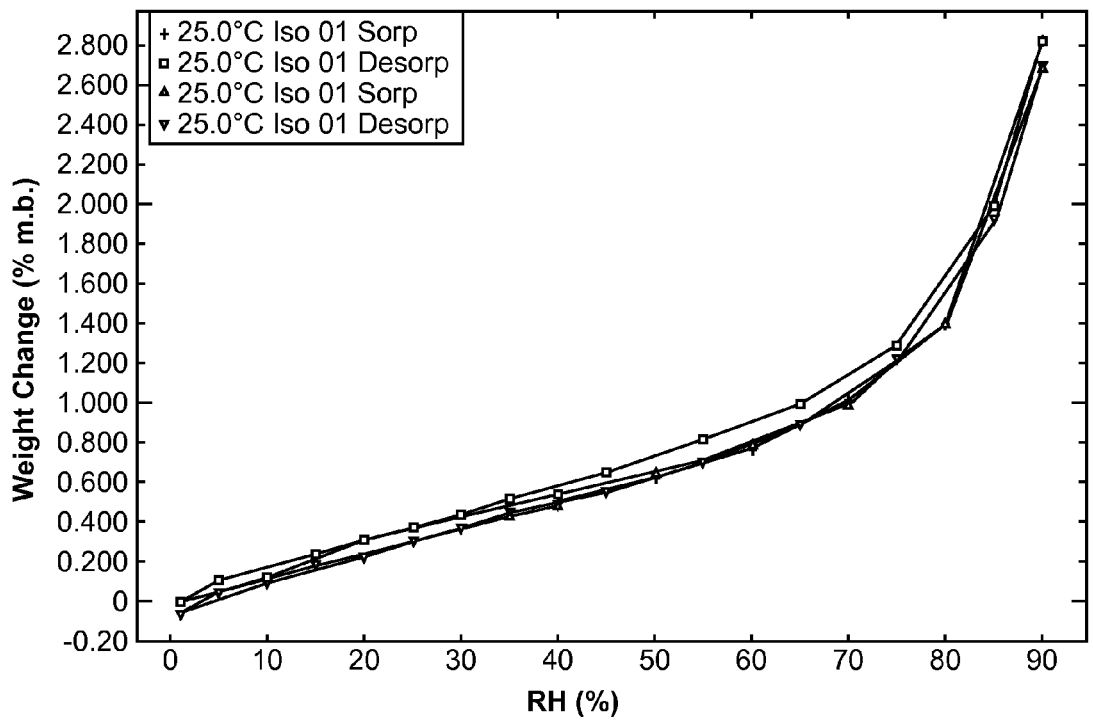
FIG. 28 provides a GVS analysis of crystalline Form A of the mesylate salt of Compound I.

Polymorphs and pseudopolymorphs can be characterized by their crystalline structure (as determined by X-ray diffraction pattern (XRPD)), their thermal properties, as determined by differential scanning calorimetry (DSC) and thermal gravimetric analysis (TGA), stability, solubility, etc. In some embodiments, Form A of the mesylate salt of Compound I is characterized by the XRPD shown in FIG. 3a, 3b or 4, the DSC data shown in FIG. 5, and/or the GVS analysis shown in FIG. 28. In some embodiments, Form B of the mesylate salt of Compound I is characterized by the X-ray diffraction pattern shown in FIG. 6 or 7 and the DSC data shown in FIG. 8a or FIG. 8b.

In some embodiments, the crystalline Form A of the mesylate salt of Compound I shows an XRPD pattern having at least four 2-theta)(2θ° peaks selected from those listed in Table 9 below. In some embodiments, the crystalline Form A of the mesylate salt of Compound I shows an XRPD pattern having at least six, eight or ten 2θ° peaks selected from those listed in Table 9 below. In some embodiments, the crystalline Form A of the mesylate salt of Compound I shows an XRPD pattern having six, eight or ten 2θ° peaks listed in Table 9 below that have the highest relative intensity. In some embodiments, the crystalline Form A of the mesylate salt of Compound I shows an XRPD pattern having all of the characteristic 2θ° peaks listed in Table 9 below. Form A of the mesylate salt of Compound I is physically stable after 6 months of storage at 40° C. and 75% RH.

In some embodiments, the crystalline form of the mesylate salt of Compound I is Form A which shows an XRPD pattern having at least four, six, eight or ten, or all of 2θ° peaks selected from the following: about 14.85, about 17.0, about 17.35, about 18.05, about 20.3, about 20.95, about 21.85, about 23.2, about 26.13, about 26.85, and about 31.75. In some embodiments, the crystalline form of the mesylate salt of Compound I is Form A which shows an XRPD pattern having at least the following 2θ° peaks: about 17.0, about 18.05, about 20.3, about 20.95, about 21.85, about 23.2, about 26.13, about 26.85, and about 31.75. In some embodiments, the crystalline form of the mesylate salt of Compound I is Form A which shows an XRPD pattern having at least the following 2θ° peaks: about 6.05, about 12.05, about 13.02, about 14.85, about 17.0, about 17.30, about 18.05, about 20.3, about 20.95, about 21.85, about 23.2, about 26.13, about 26.85, about 29.55, and about 31.75. In some embodiments, the crystalline form of the mesylate salt of Compound I is Form A which shows an XRPD pattern substantially the XRPD pattern as FIG. 3 and/or a DSC pattern substantially the DSC pattern as FIG. 5. In some embodiments, the crystalline form of the mesylate salt of Compound I is Form A which shows a GVS analysis substantially the GVS analysis represented by FIG. 28.

In some embodiments, the crystalline Form B of the mesylate salt of Compound I is a hydrate. In some embodiments, Form B shows an XRPD pattern having at least four 2θ° peaks selected from those listed in Table 10 below. In some embodiments, the crystalline Form B of the mesylate salt of Compound I shows an XRPD pattern having at least six, eight or ten 2-theta (2θ°) peaks selected from those listed in Table 10 below. In some embodiments, the crystalline Form B of the mesylate salt of Compound I shows an XRPD pattern having six, eight or ten 2θ° peaks listed in Table 10 below that have the highest relative intensity. In some embodiments, the crystalline Form B of the mesylate salt of Compound I shows an XRPD pattern having the characteristic 2θ° peaks listed in Table 10 below.

In some embodiments, the crystalline form of the mesylate salt of Compound I is Form B which shows an XRPD pattern having at least four, six, eight or ten of the following 2θ° peaks: about 12.35, about 13.97, about 16.96, about 18.95, about 20.41, about 21.85, about 22.75, about 25.65, about 25.75, and about 26.65. In some embodiments, the crystalline form of the mesylate salt of Compound I is Form B which shows an XRPD pattern having at least the following 2θ° peaks: about 12.35, about 13.97, about 16.96, about 18.95, about 21.30, about 21.85, about 22.75, about 25.75 and about 26.65. In some embodiments, the crystalline form of the mesylate salt of Compound I is Form B which shows an XRPD pattern having at least the following 2θ° peaks: about 12.35, about 13.97, about 16.96, about 18.95, about 21.30, about 21.85, about 22.75, about 24.35, about 25.75 and about 26.65. In some embodiments, the crystalline form of the mesylate salt of Compound I is Form B which shows an XRPD pattern substantially the XRPD pattern as FIG. 6 and/or a DSC pattern substantially the DSC pattern as FIG. 8a or 8b.

One skilled in the art would understand that the height of the peak and relative intensity are reliant on many experimental conditions including the type of instrument, beam intensity, length of acquisition time, sample preparation, etc. The 2θ° peaks provided herein may vary within ±0.2 2θ°, ±0.1 2θ°, ±0.05 2θ°, or ±0.02 2θ°. When two XRDP patterns have at least 4, at least 6, 8, or 10 2θ° peaks, that do not vary more than ±5%, or ±1%, or ±0.2% in position and optionally in intensity, it is deemed that the XRDP patterns are substantially the same. In one embodiments, the 4, 6, 8, or 10 peaks are the peaks that have the highest intensity.

Figure 5:
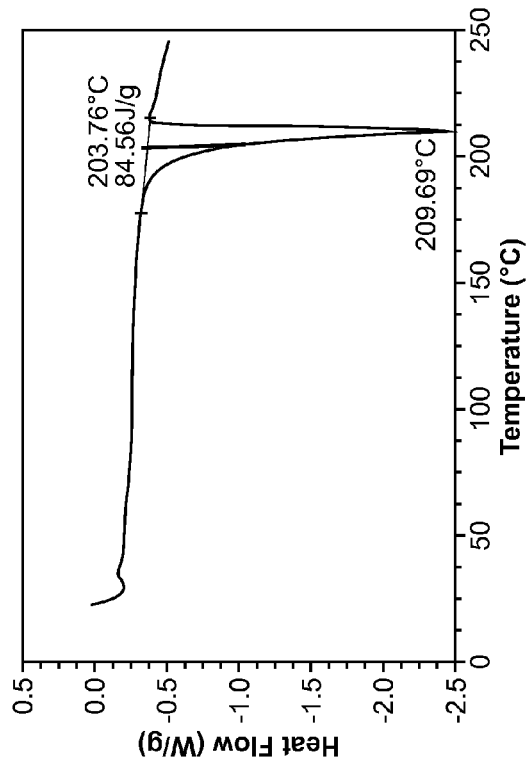
FIG. 5 provides a differential scanning calorimetry (DSC) scan of crystalline Form A of the mesylate salt of Compound I.
Figure 6:
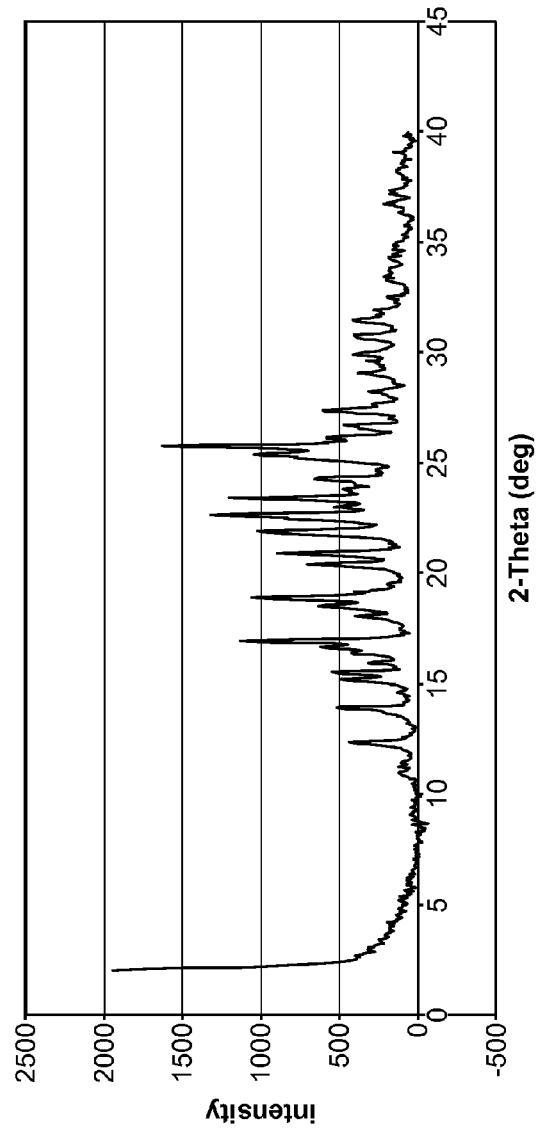
FIG. 6 provides an XRPD pattern of crystalline Form B of the mesylate salt of Compound I.
Figure 8A:
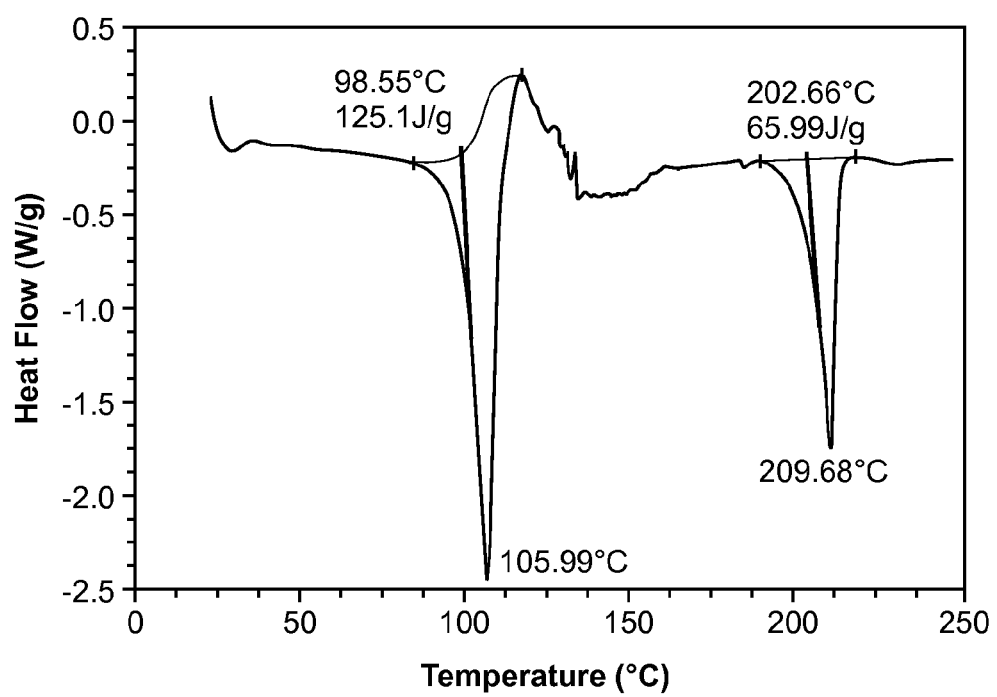
FIGS. 8a and 8b provide DSC scans of different samples crystalline Form B of the mesylate salt of the compound of Formula. The second peak at about 209° C.
Figure 8B:
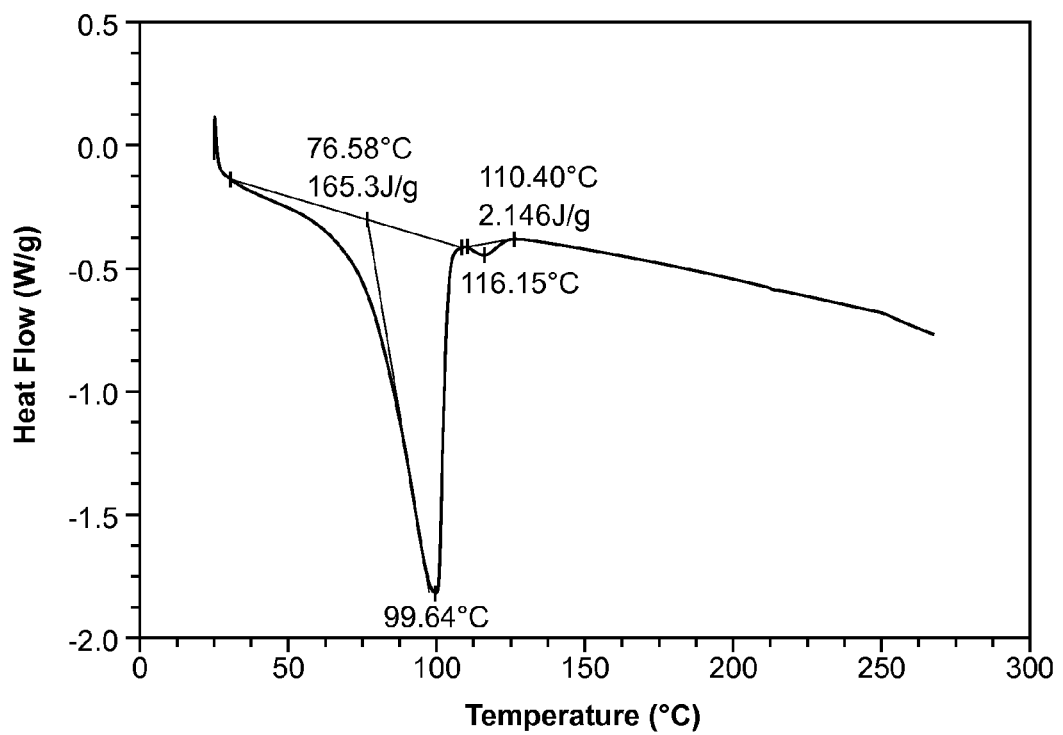
Figure 9:
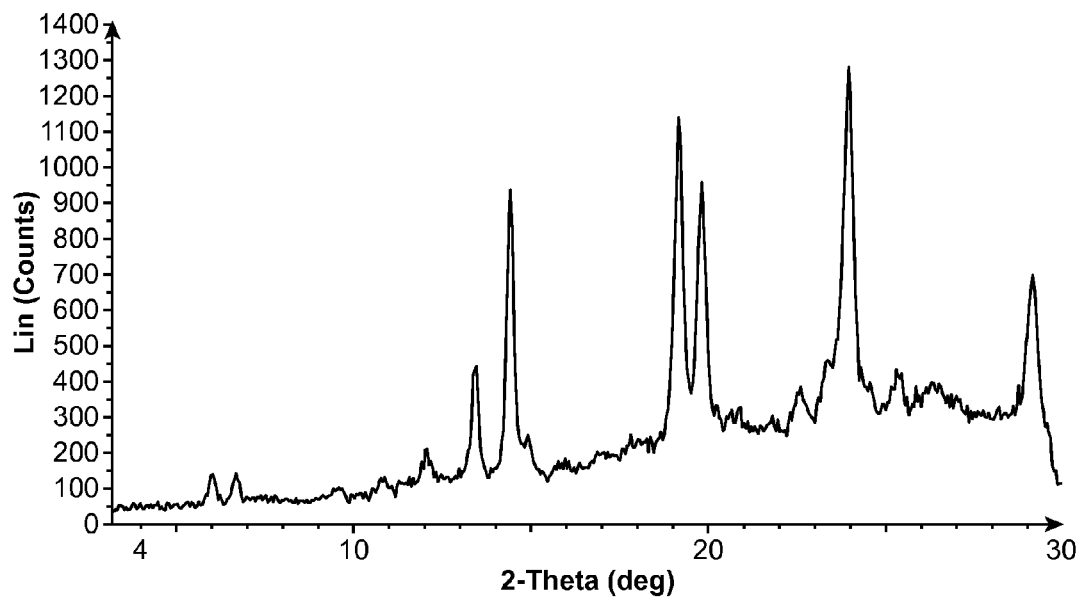
FIG. 9 provides an XRPD pattern of Compound I free base.

In some embodiments, the crystalline forms of the mesylate salt of Compound I show a DSC pattern substantially the same as the DSC patterns in FIG. 5, 8a or 8b. When two DSC patterns have peaks that do not vary more than ±5%, or ±1%, or ±0.2% in position (° C.) and optionally in intensity, it is deemed that the DSC patterns are substantially the same.

In one aspect, this invention provides a method for preparing the crystalline Form A of the mesylate salt of Compound I comprising mixing the free base of Compound I with at least one equivalent of methanesulfonic acid in a solvent comprising methylethyl ketone, and optionally tetrahydrofuran. In some embodiments, the method further comprises heating the mixture to a temperature of at or above about 50° C. and cool to a temperature of at about 20° C. In some embodiments, the method further comprises recovering the crystalline Form A.

In one aspect, this invention provides a method for preparing the crystalline Form B of the mesylate salt of Compound I comprising recrystallizing a mesylate salt of Compound I in a solvent comprising acetone and optionally water. In some embodiments, the method further comprises heating the mixture to a temperature of at or above about 55-60° C. and cool to a temperature of at about 20±5° C. In some embodiments, the method further comprises recovering the crystalline Form B.

In another aspect, there is provided a mesylate salt of Compound I wherein at least a portion of the mesylate salt is in crystalline Form A and/or Form B. In some embodiments, about or greater than 50% by weight of the mesylate salt of Compound I is present as the polymorphic Form A and/or B. In some embodiments, about or greater than 60% by weight; about or greater than 65% by weight; about or greater than 70% by weight; about or greater than 75% by weight; about or greater than 80% by weight; about or greater than 85% by weight; about or greater than 90% by weight; about or greater than 95% by weight; or about or greater than 99% by weight of the mesylate salt of Compound I is present in the composition as the crystalline Form A and/or B.

In another aspect, this invention is directed to a 1-hydroxy-2-napthoate salt of Compound I.

In one embodiment, the 1-hydroxy-2-naphthoate salt of Compound I is of the formula:

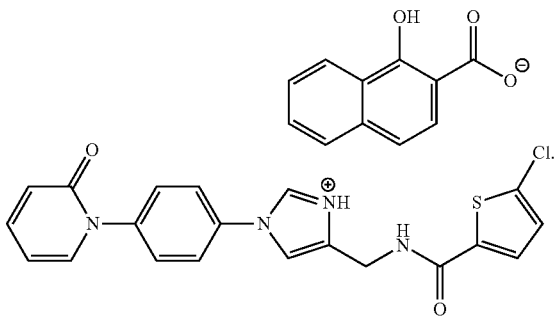 [SMILES: O=C([O-])c1ccc2ccccc2c1O ; O=C(NCc1cn(-c2ccc(-n3ccccc3=O)cc2)c[nH+]1)c1ccc(Cl)s1]

"The 1-hydroxy-2-naphthoate salt of Compound I" refers to the salt formed between Compound I and 1-hydroxy-2-naphthoic acid, in an equivalent ratio of, for example, about 1 to 1.

Figure 10A:
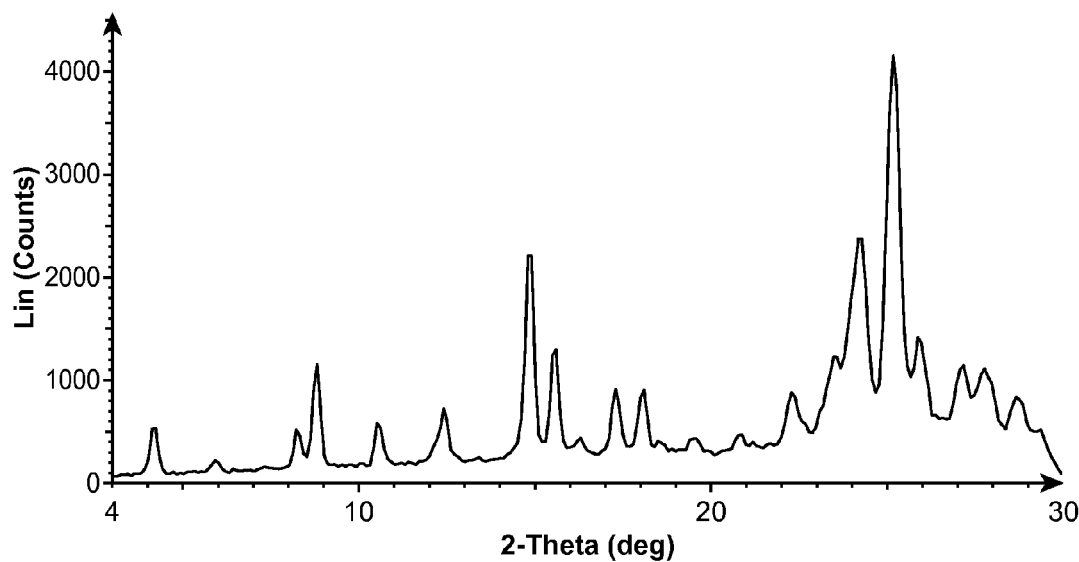
FIG. 10a provides an XRPD pattern of a crystalline form of a 1-hydroxy-2-naphthoate salt of Compound I.
Figure 10B:
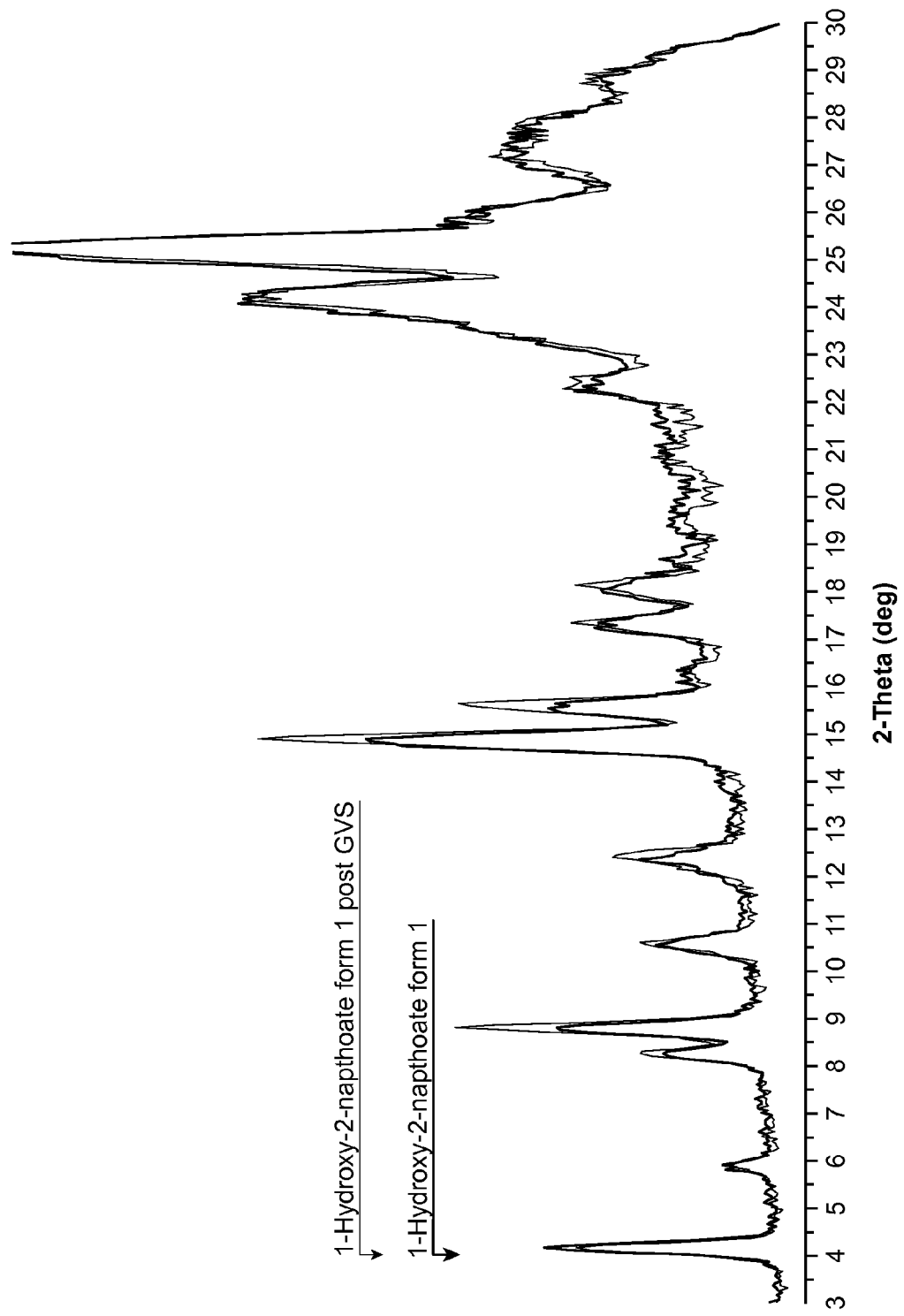
FIG. 10b provides an XRPD pattern of a crystalline form of a 1-hydroxy-2-naphthoate salt of Compound I pre and post GVS.
Figure 11:
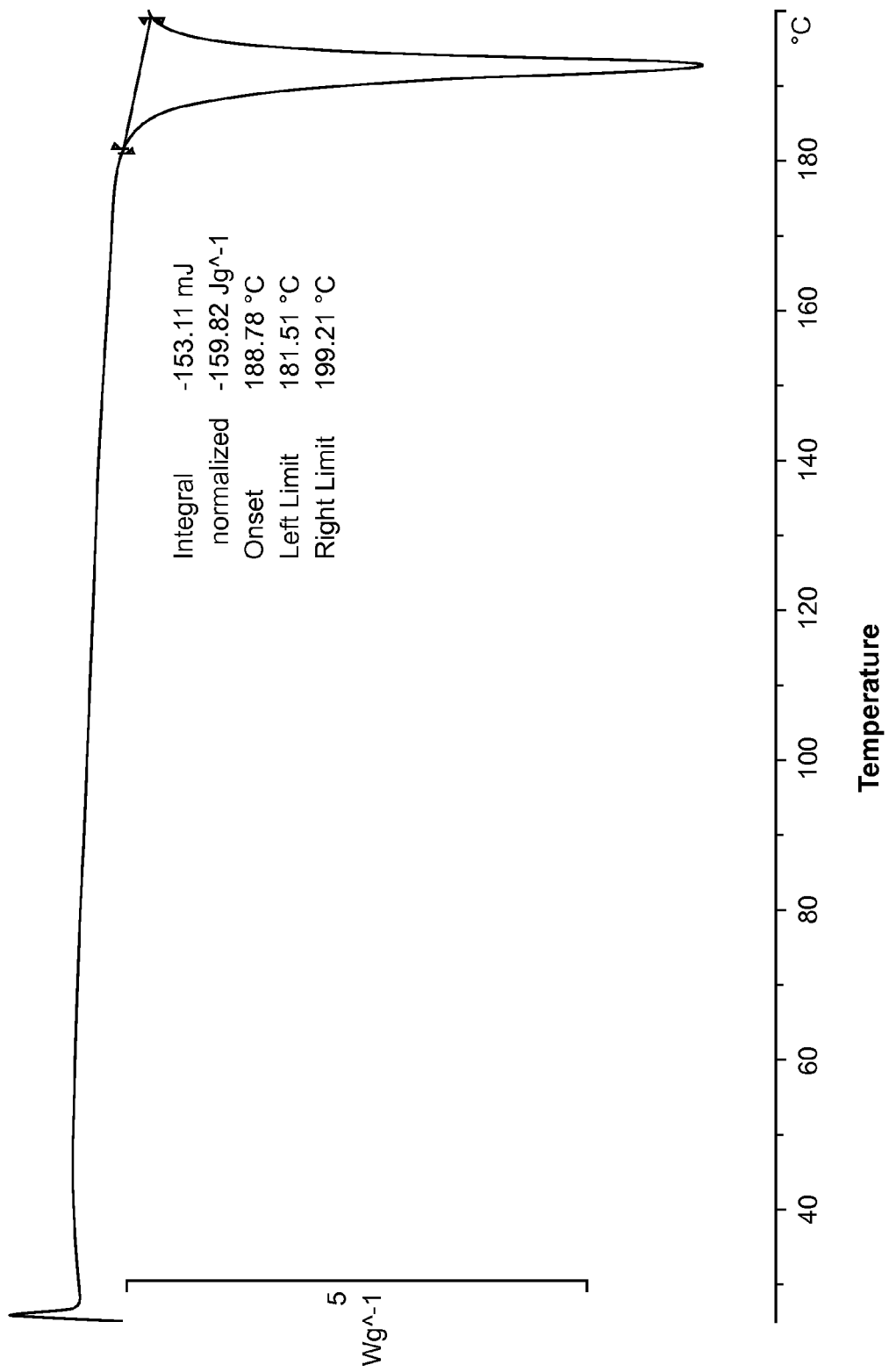
FIG. 11 provides a differential scanning calorimetry (DSC) scan for a crystalline form of the 1-hydroxy-2-naphthoate salt of Compound I.
Figure 21:
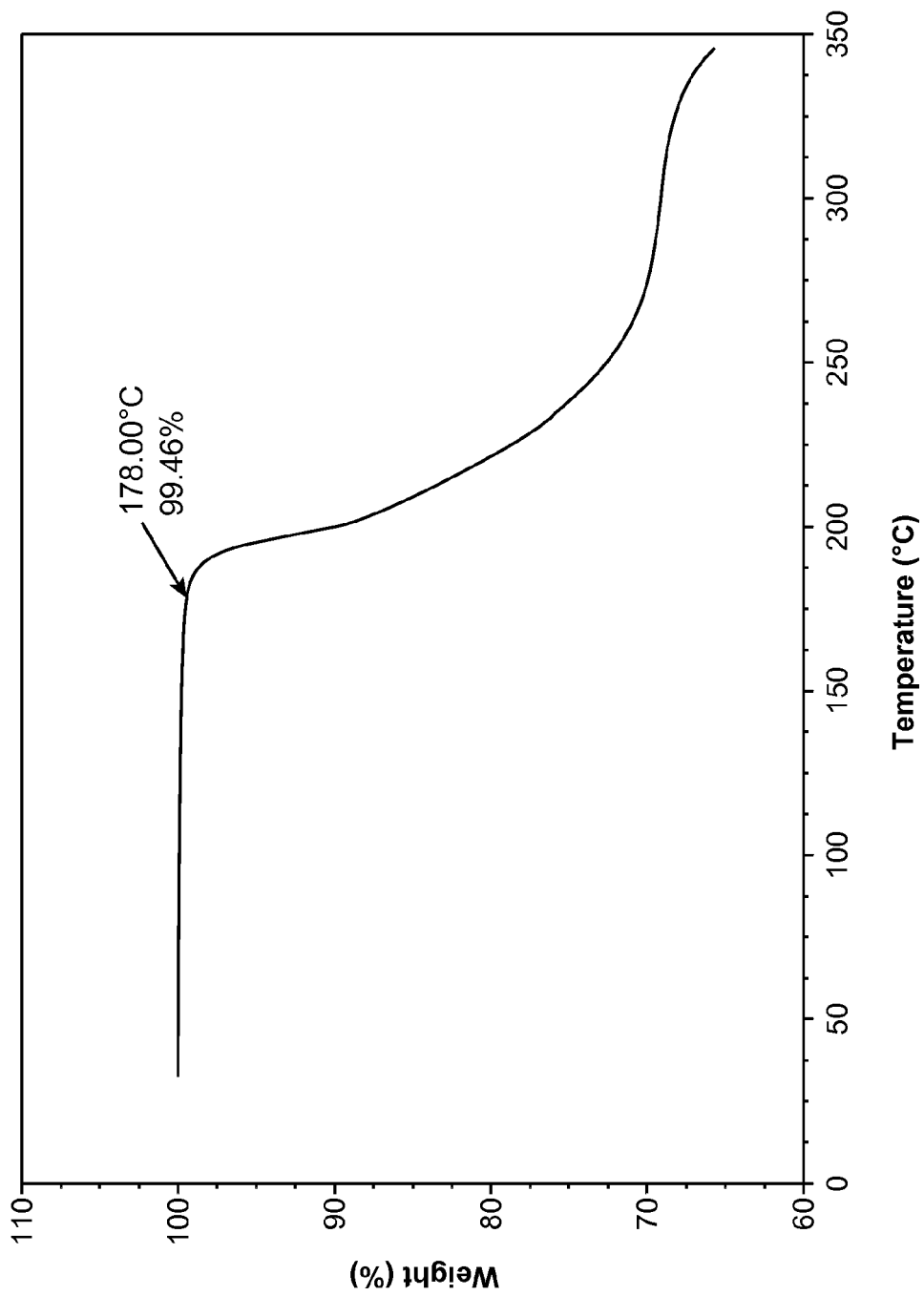
FIG. 21 provides a TGA analysis of a crystalline form of 1-hydroxy-2-naphthoate salt of Compound I.
Figure 22:
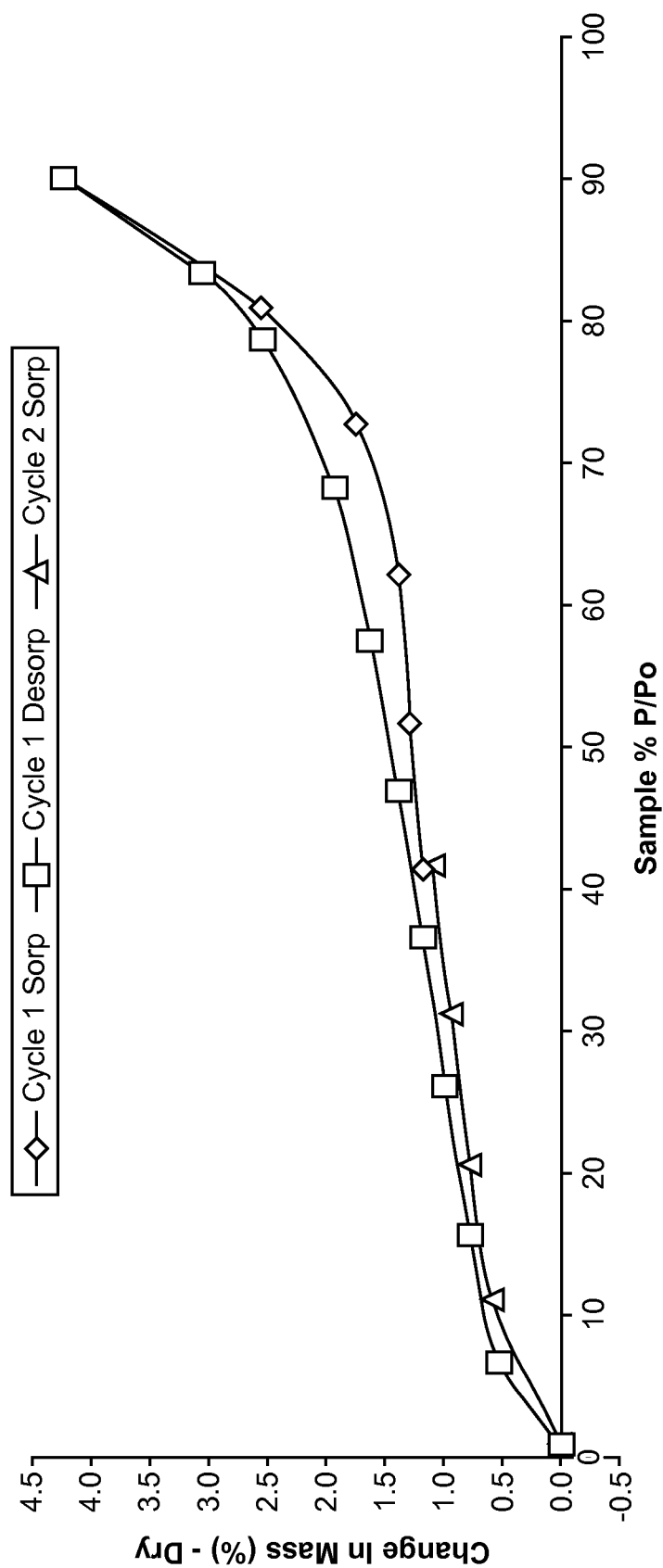
FIG. 22 provides a GVS isotherm plot of a crystalline form of 1-hydroxy-2-naphthoate salt of Compound I.

The 1-hydroxy-2-naphthoate salt may exist in an amorphous form or in a crystalline form or mixture of an amorphous form and a crystalline form or a mixture of several polymorphic or pseudopolymorphic forms. In some embodiments, the crystalline form of the 1-hydroxy-2-naphthoate salt of Compound I shows an XRPD pattern having at least four, six, eight, or ten, or all of the following 2θ° peaks: about 4.3, about 6, about 8.45, about 9, about 10.5, about 12.5, about 15.0, about 15.7, about 17.4, about 18.45, about 24.3, and about 25.05. In some embodiments, at least a portion of the salt is in a crystalline form. In some embodiments, the crystalline form of the 1-hydroxy-2-naphthoate salt of Compound I shows an XRPD pattern which is substantially the same as the XRPD pattern of FIG. 10a. FIG. 10b shows an overlay of the XRPD pattern pre and post GVS, indicating that the crystalline form of the 1-hydroxy-2-naphthoate salt of Compound I is substantially stable after being exposed to moisture. In some embodiments, the crystalline form of Compound I 1-hydroxy-2-naphthoate salt shows a TGA, DSC, and/or GVS analysis substantially the same as the TGA, DSC, and GVS analysis represented by FIGS. 21, 11, and 22, respectively.

In another aspect, at least a portion of the 1-hydroxy-2-naphthoate salt of Compound I is in the crystalline form. In some embodiments, about or greater than 50% by weight of the 1-hydroxy-2-naphthoate salt of Compound I is in the crystalline form. In some embodiments, about or greater than 60% by weight; about or greater than 65% by weight; about or greater than 70% by weight; about or greater than 75% by weight; about or greater than 80% by weight; about or greater than 85% by weight; about or greater than 90% by weight; about or greater than 95% by weight; or about or greater than 99% by weight of the 1-hydroxy-2-naphthoate salt of Compound I is in the crystalline form.

In another aspect, this invention provides a crystalline form of a phosphate salt of Compound I. In some embodiments, the phosphate salt of Compound I is of the formula:

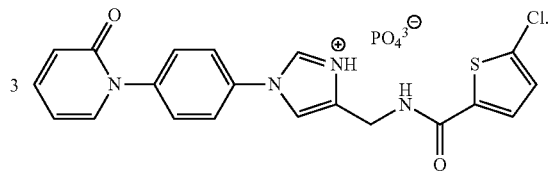 [SMILES: O=C(NCc1cn(-c2ccc(-n3ccccc3=O)cc2)c[nH+]1)c1ccc(Cl)s1]

In some embodiments, the phosphate salt of Compound I is of the formula:

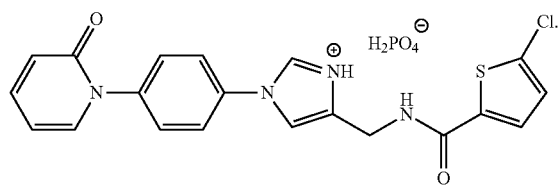 [SMILES: O=C(NCc1cn(-c2ccc(-n3ccccc3=O)cc2)c[nH+]1)c1ccc(Cl)s1 ; "H2PO4"]

"The phosphate salt of Compound I" refers the salt formed between Compound I and phosphoric acid ($H_3PO_4$), in an equivalent ratio of, for example, about 1 to 1.

The phosphate salt may exist in an amorphous form or in a crystalline form or mixture of an amorphous form and a crystalline form or a mixture of several polymorphic and/or pseudopolymorphic forms. In some embodiments, at least a portion of the salt is in a crystalline form.

Figure 12:
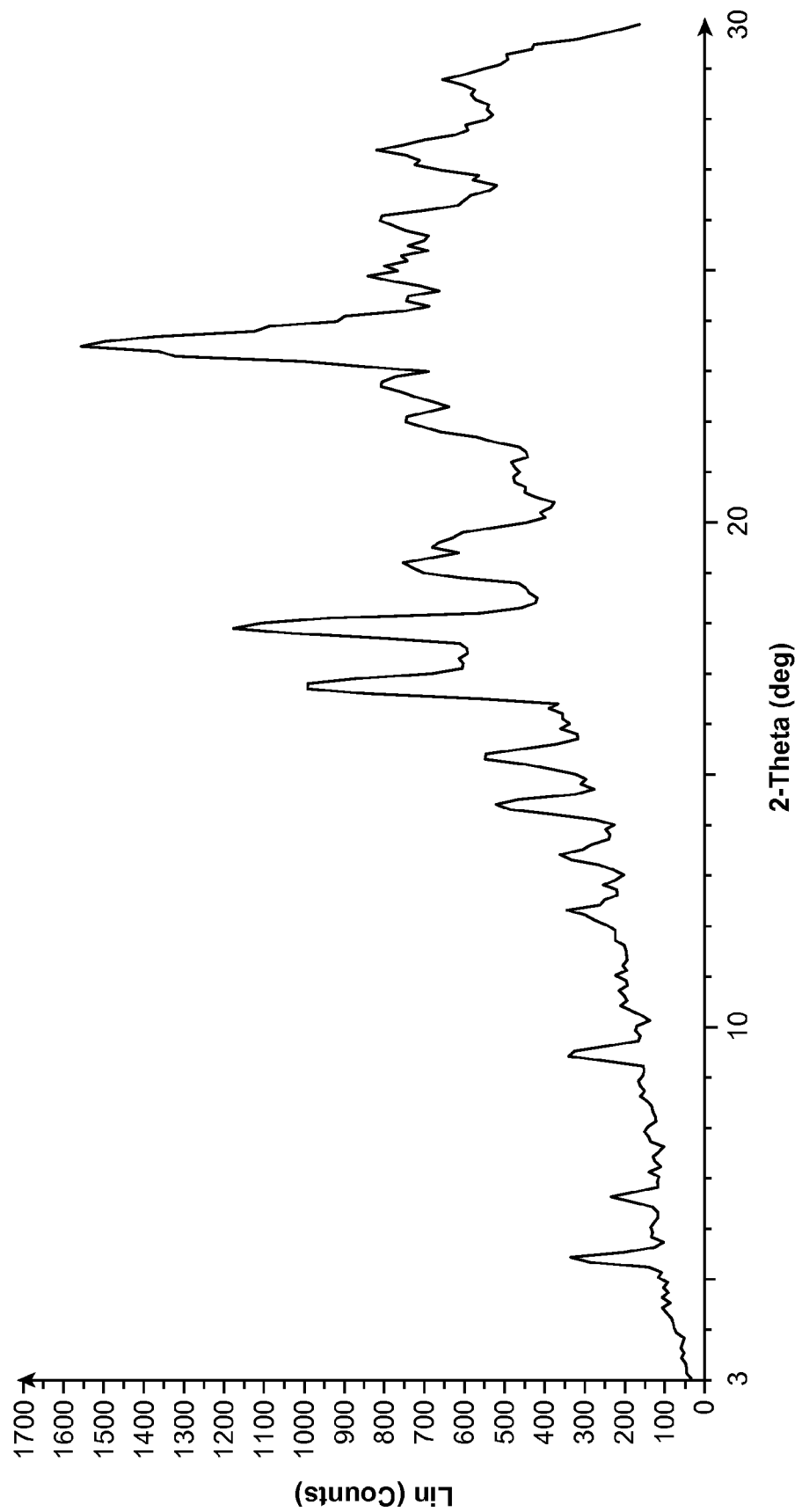
FIG. 12 provides an XRPD pattern of a crystalline Form 1 of the phosphate salt of Compound I.

In some embodiments, the crystalline form of the phosphate salt Compound I is Form 1 and shows an XRPD pattern having at least four, six, eight, or ten, or all of the following 2θ° peaks: about 5.4, about 6.5, about 9.5, about 14.7, about 15.6, about 16.8, about 17.9, about 19.2, about 22.2, about 22.8, and about 23.65. In some embodiments, the crystalline form of the phosphate salt of Compound I is Form 1 and shows an XRPD pattern which is substantially the same as the XRPD pattern of the FIG. 12. Form 1 was not reproduced when scaled up.

Figure 13:
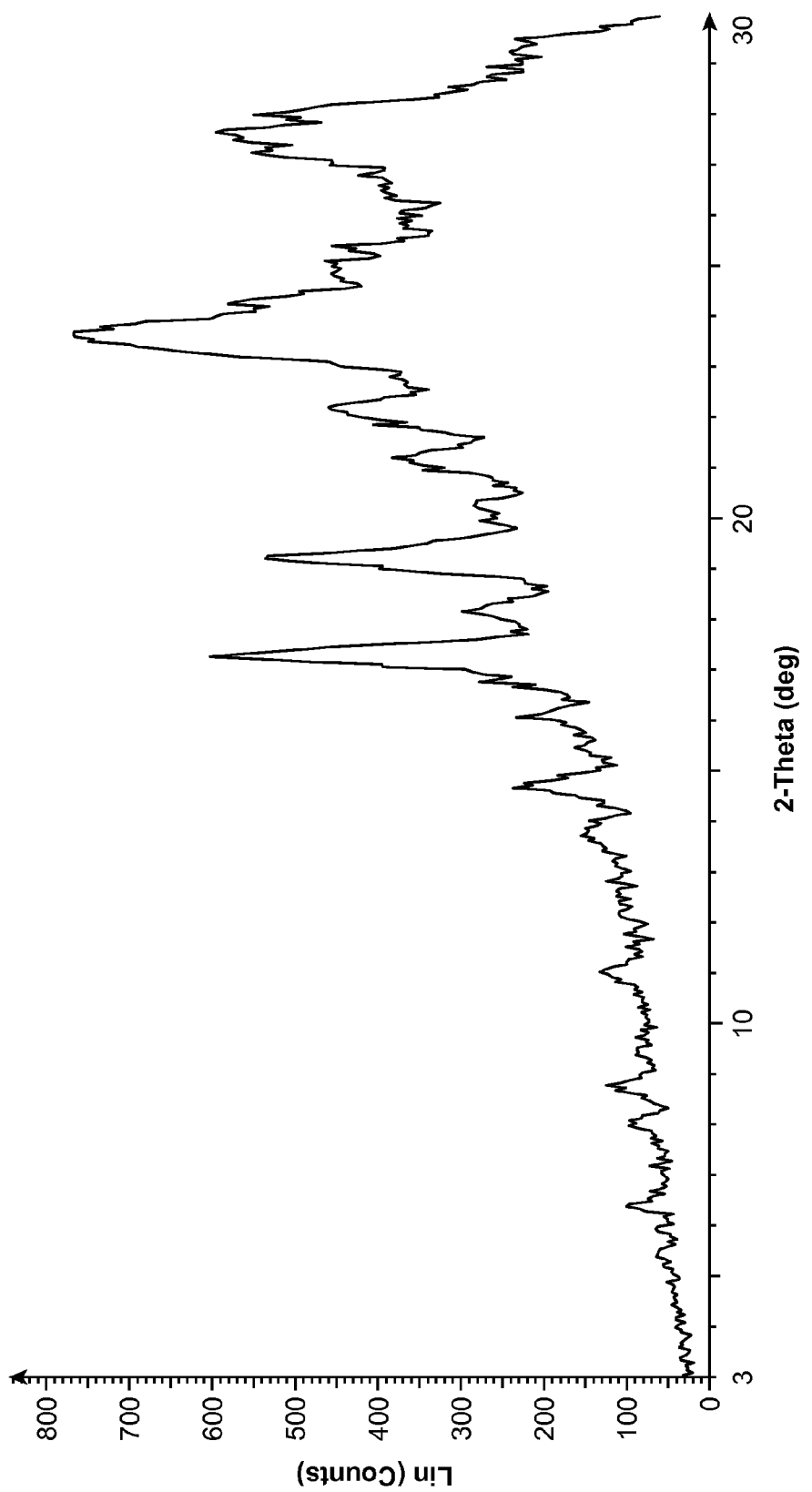
FIG. 13 provides an XRPD pattern of a sample of a crystalline Form 2 of the phosphate salt of Compound I, which sample is not particularly crystalline and may be of limited representation of Form 2 of the phosphate salt.
Figure 23:
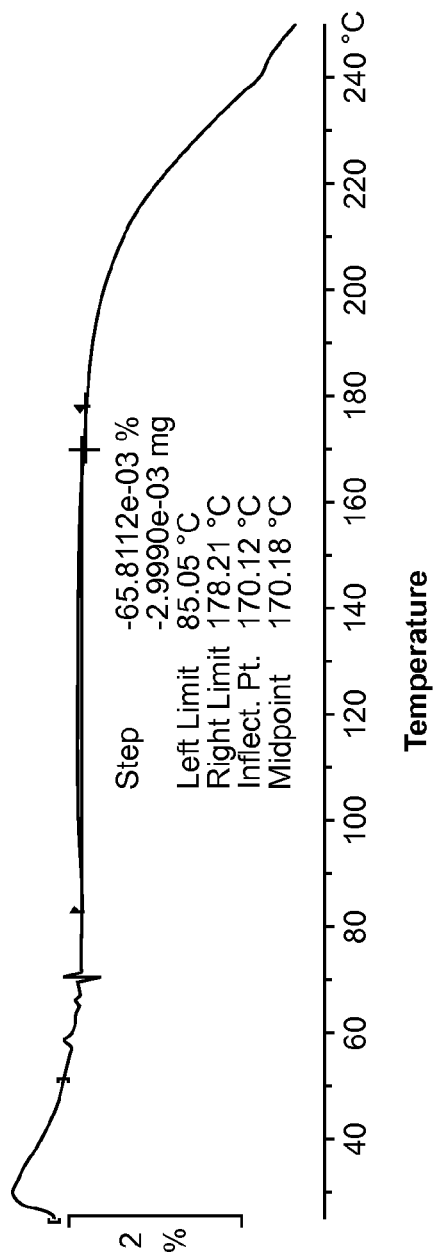
FIG. 23 provides a TGA analysis of the crystalline Form 2 of the phosphate salt of Compound I.
Figure 24:
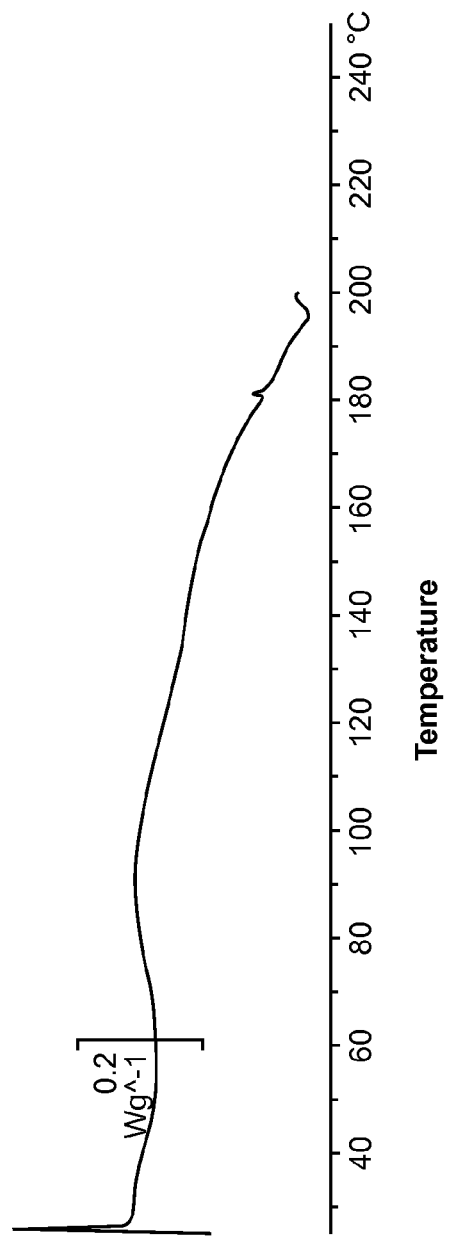
FIG. 24 provides a DSC analysis of the crystalline Form 2 of the phosphate salt of Compound I.
Figure 25:
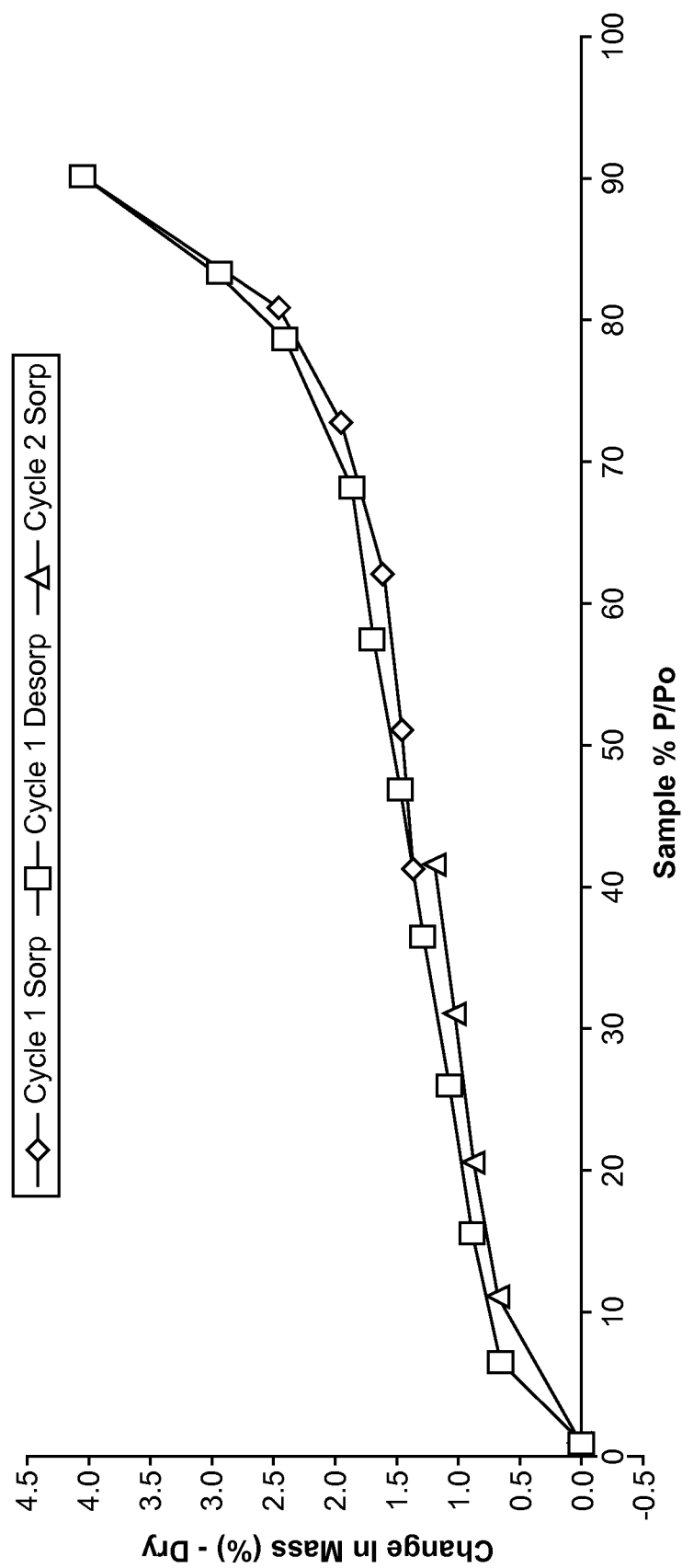
FIG. 25 provides a GVS isotherm plot of the crystalline Form 2 of the phosphate salt of Compound I.

In some embodiments, the crystalline form of the phosphate salt of Compound I is Form 2 and shows an XRPD pattern having at least four, six, or all of the following 2θ° peaks: about 6.5, about 8, about 8.8, about 11.0, about 14.5, about 17.3, and about 18.2. In some embodiments, the crystalline form of the phosphate salt of Compound I is Form 2 and shows an XRPD pattern which is substantially the same as the XRPD pattern of the FIG. 13. In some embodiments, the crystalline Form 2 of Compound I phosphate salt shows a TGA, DSC and/or GVS analysis substantially the same as the TGA, DSC and GVS analysis represented by FIGS. 23, 24 and 25, respectively.

Figure 14:
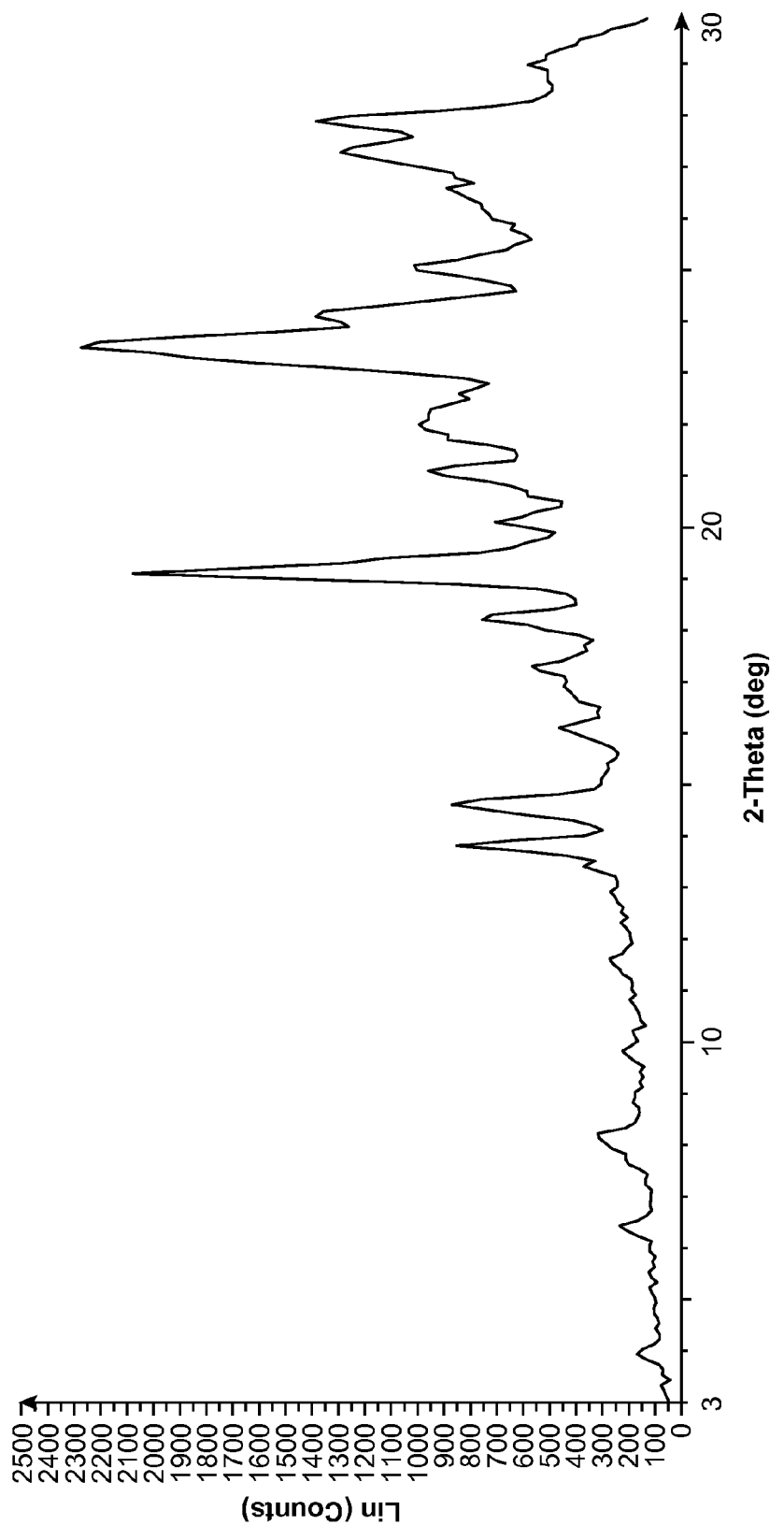
FIG. 14 provides an XRPD pattern of a crystalline Form 3 of the phosphate salt of Compound I.
Figure 18:
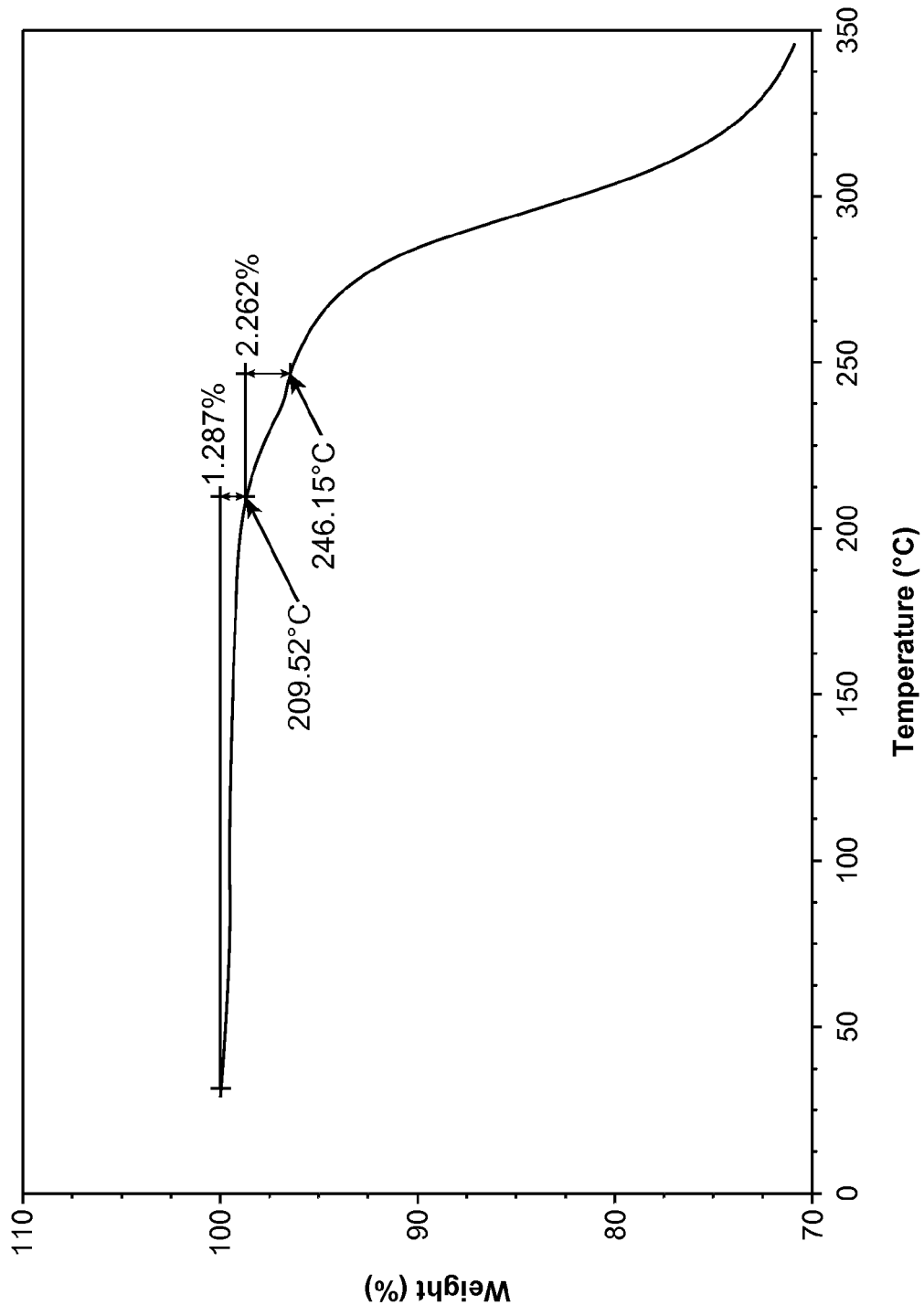
FIG. 18 provides a TGA analysis of the crystalline Form 3 of the phosphate salt of Compound I.
Figure 19:
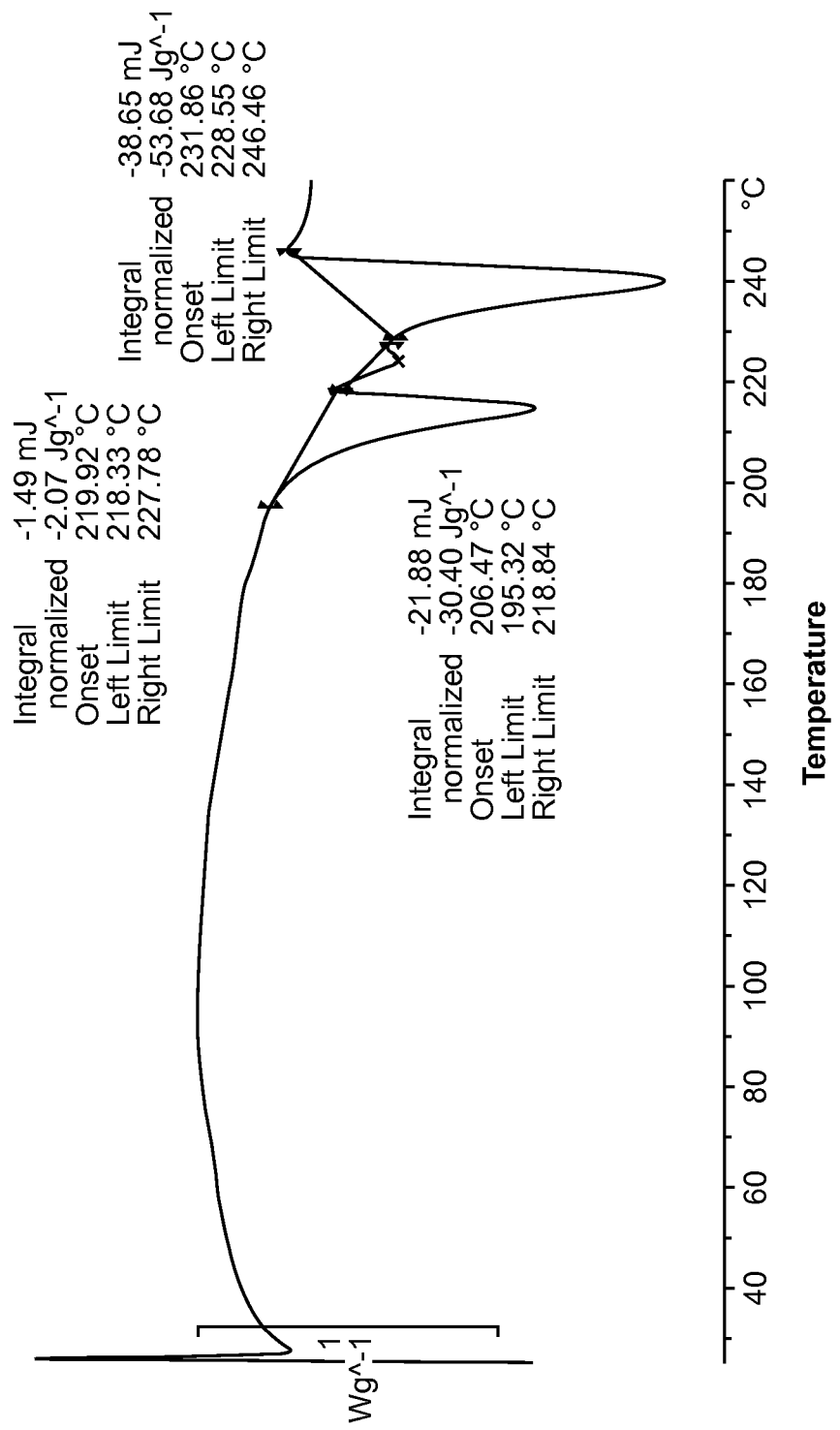
FIG. 19 provides a DSC analysis of the crystalline Form 3 of the phosphate salt of Compound I.
Figure 20:
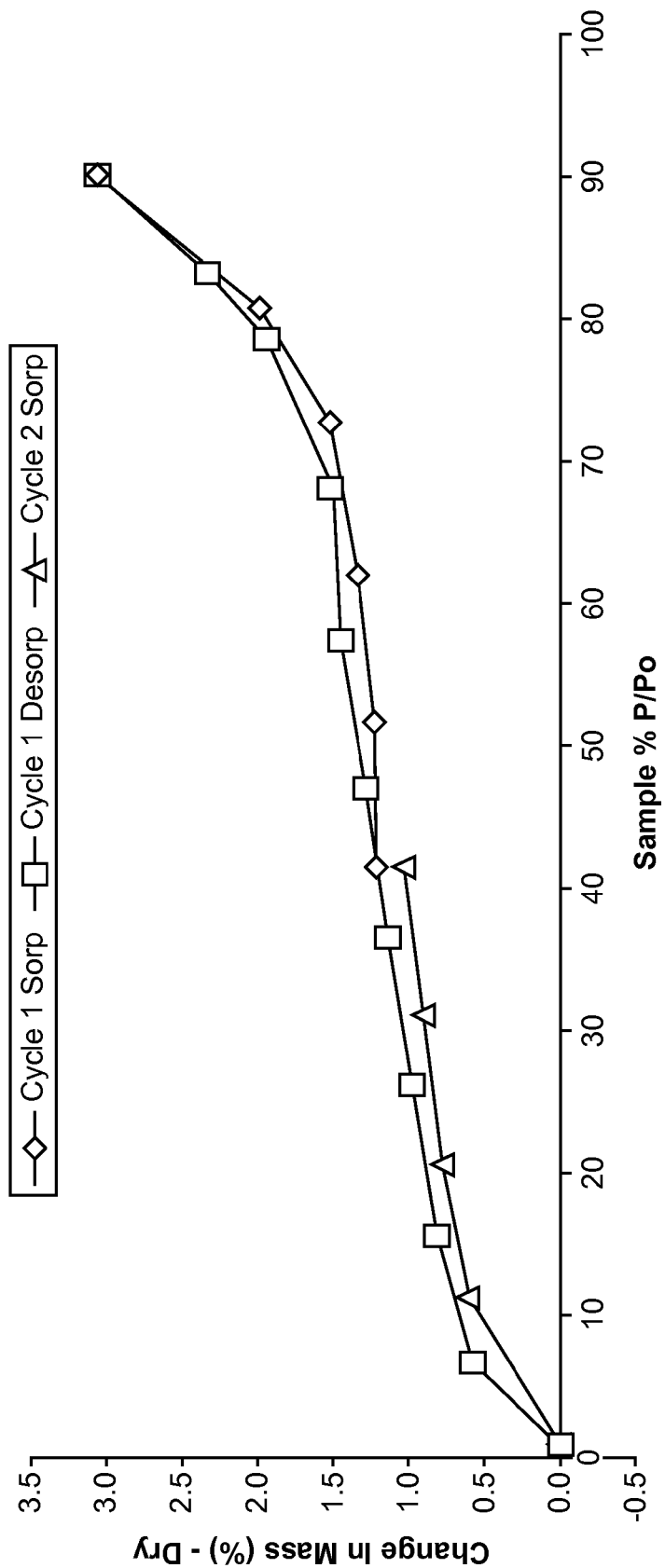
FIG. 20 provides a GVS isotherm plot of the crystalline Form 3 of the phosphate salt of Compound I.

In some embodiments, the crystalline form of the phosphate salt of Compound I is Form 3 and shows an XRPD pattern having at least four, six, eight, or ten, or all of the following 2θ° peaks: about 4, about 6.5, about 8.2, about 13.9, about 14.5, about 16, about 17.45, about 18.2, about 19.15, about 20.1, about 21.45, about 22.35, about 23.5, about 24.0, about 25.2, about 27.65, and about 28.25. In some embodiments, the crystalline form of the phosphate salt of Compound I is Form 3 and shows an XRPD pattern which is substantially the same as the XRPD pattern of the FIG. 14. In some embodiments, the crystalline Form 3 of Compound I phosphate salt shows a TGA, DSC and/or GVS analysis substantially the same as the TGA, DSC and GVS analysis represented by FIGS. 18, 19 and 20, respectively.

In another aspect, this invention is directed to a phosphate salt of Compound I wherein at least a portion of the phosphate salt is in crystalline Forms 1, 2, and/or 3. In some embodiments, about or greater than 50% by weight of the phosphate salt of Compound I is present as the polymorphic Forms 1, 2, and/or 3. In some embodiments, about or greater than 60% by weight; about or greater than 65% by weight; about or greater than 70% by weight; about or greater than 75% by weight; about or greater than 80% by weight; about or greater than 85% by weight; about or greater than 90% by weight; about or greater than 95% by weight; or about or greater than 99% by weight of the phosphate salt of Compound I is present in the composition as the crystalline Forms 1, 2, and/or 3.

In another embodiment, the thiocyanate salt of Compound I is of the formula:

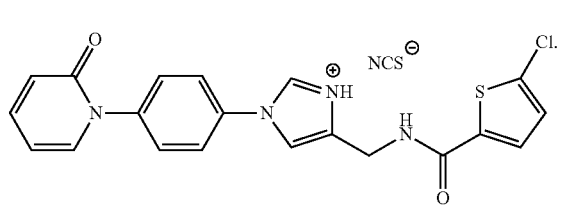

"The thiocyanate salt of Compound I" refers the salt formed between Compound I and thiocyanic acid (NCSH), in an equivalent ratio of, for example, about 1 to 1.

Figure 15:
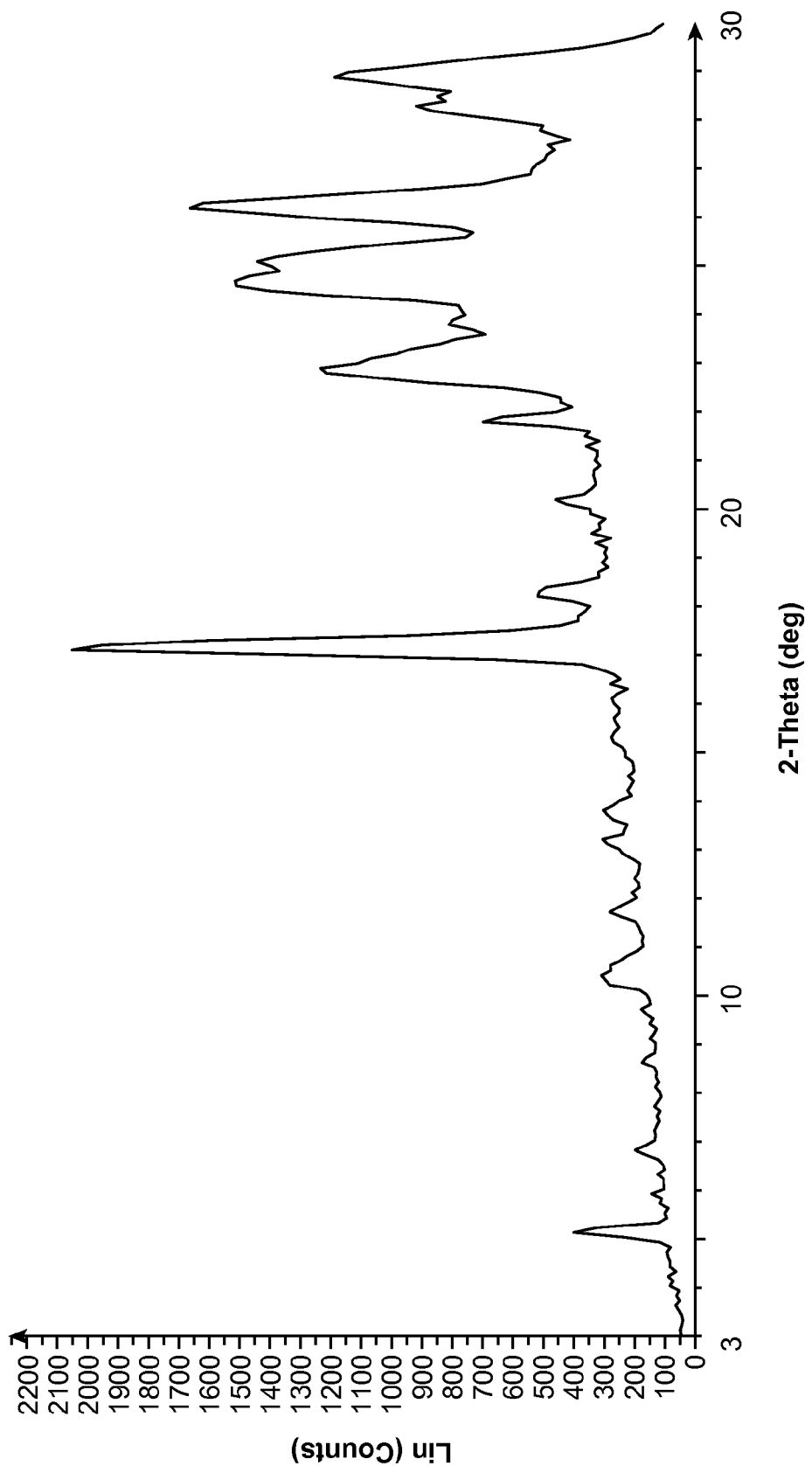
FIG. 15 provides an XRPD pattern of a crystalline form of the thiocyanate salt of Compound I.

In another embodiment, this invention provides a thiocyanate salt of Compound I. The thiocyanate salt may exist in an amorphous form or in a crystalline form or mixture of an amorphous form and a crystalline form or a mixture of several polymorphic forms. In some embodiments, the crystalline form of the thiocyanate salt Compound I shows an XRPD pattern having at least four, six, eight, or ten, or all of the following 2θ° peaks: about 5.0, about 10.5, about 11.8, about 13.5, about 14.0, about 17.45, about 18.3, about 21.95, about 23.0, about 24.5, about 25.0, about 26.2, about 28.5, and about 29.0. In some embodiments, at least a portion of the salt is in a crystalline form. In some embodiments, the crystalline form of the thiocyanate salt of Compound I shows an XRPD pattern which is substantially the same as the XRPD pattern of FIG. 15.

In another aspect, at least a portion of the thiocyanate salt of Compound I is in the crystalline form. In some embodiments, about or greater than 50% by weight of the thiocyanate salt of Compound I is in the crystalline form. In some embodiments, about or greater than 60% by weight; about or greater than 65% by weight; about or greater than 70% by weight; about or greater than 75% by weight; about or greater than 80% by weight; about or greater than 85% by weight; about or greater than 90% by weight; about or greater than 95% by weight; or about or greater than 99% by weight of the thiocyanate salt of Compound I is in the crystalline form.

Figure 17:
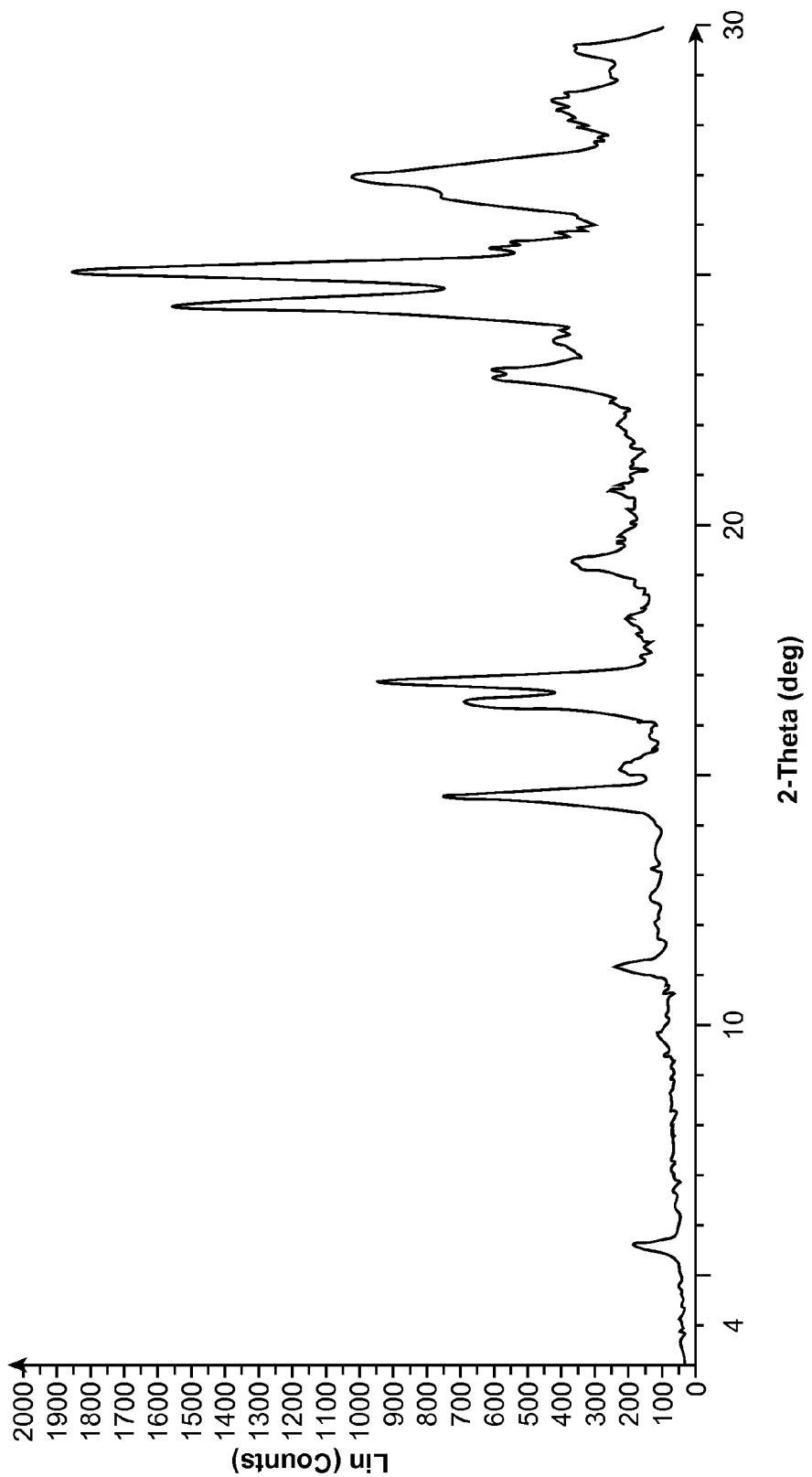
FIG. 17 provides an XRPD pattern of a crystalline form of the maleate salt of Compound I.
Figure 26:
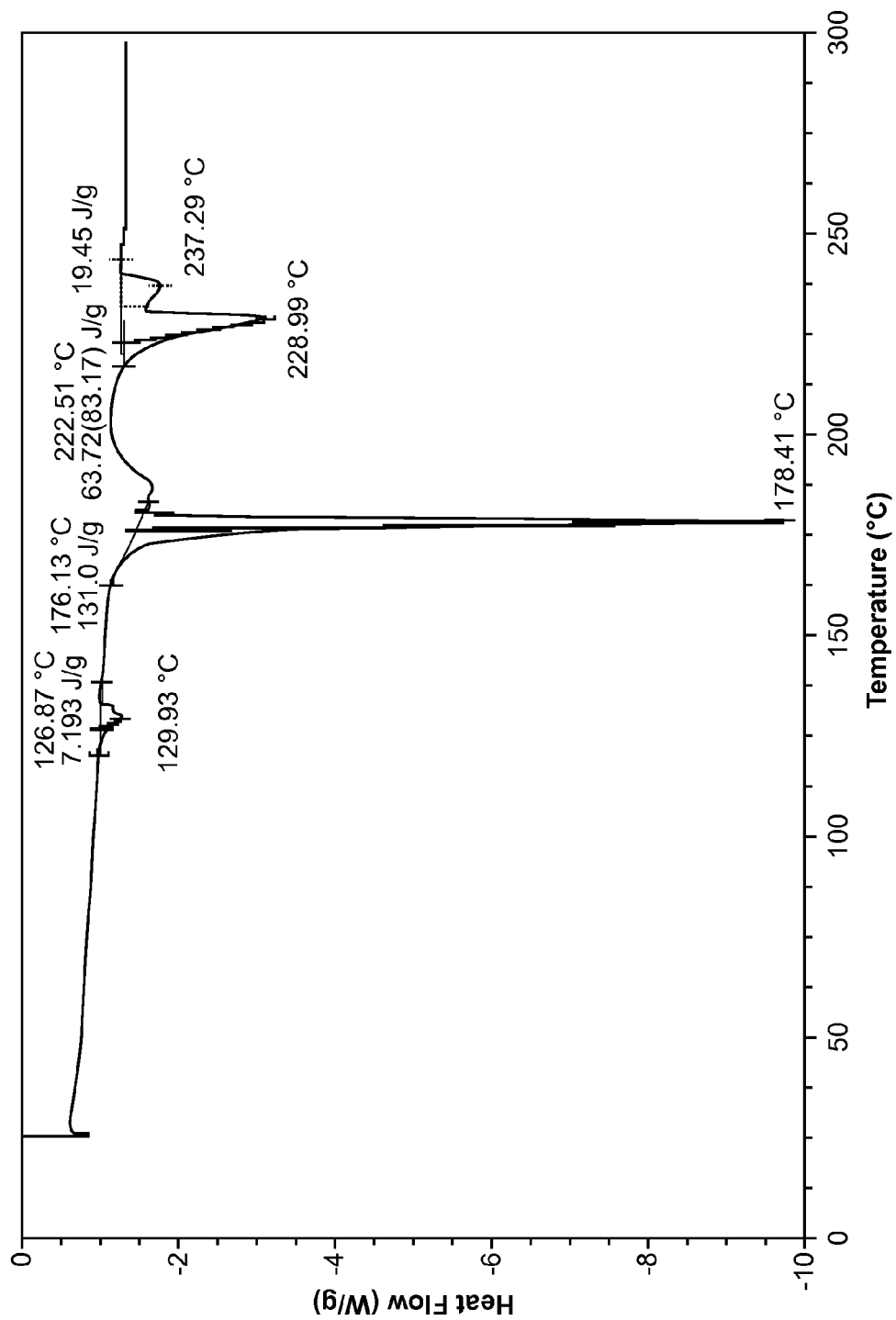
FIG. 26 provides a DSC analysis of the crystalline of the maleate salt of Compound I.
Figure 27:
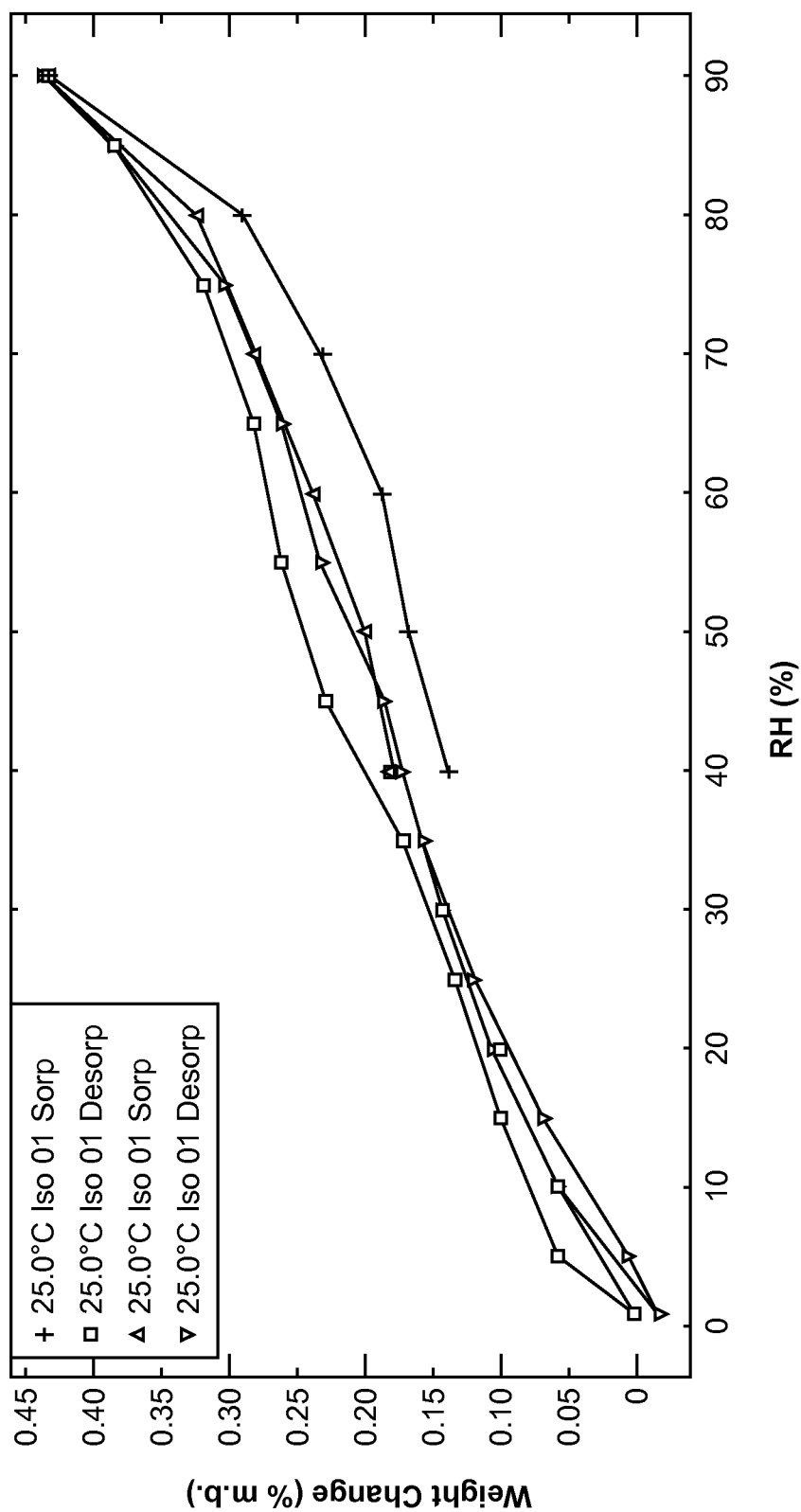
FIG. 27 provides a GVS analysis of the crystalline of the maleate salt of Compound I.

In another embodiment, this invention provides a crystalline form of a maleate salt of Compound I. In some embodiments, the crystalline form of the maleate salt of Compound I shows an XRPD pattern which is substantially the same as the XRPD pattern of FIG. 17. In some embodiments, the crystalline form of Compound I maleate salt shows a DSC and/or GVS analysis substantially the same as the DSC and GVS analysis represented by FIGS. 26 and 27, respectively.

In another aspect, at least a portion of the maleate salt of Compound I is in the crystalline form. In some embodiments, about or greater than 50% by weight of the maleate salt of Compound I is in the crystalline form. In some embodiments, about or greater than 60% by weight; about 65% by weight; about or greater than 70% by weight; about or greater than 75% by weight; about or greater than 80% by weight; about or greater than 85% by weight; about or greater than 90% by weight; about or greater than 95% by weight; or about or greater than 99% by weight of the maleate salt of Compound I is in the crystalline form.

Figure 16:
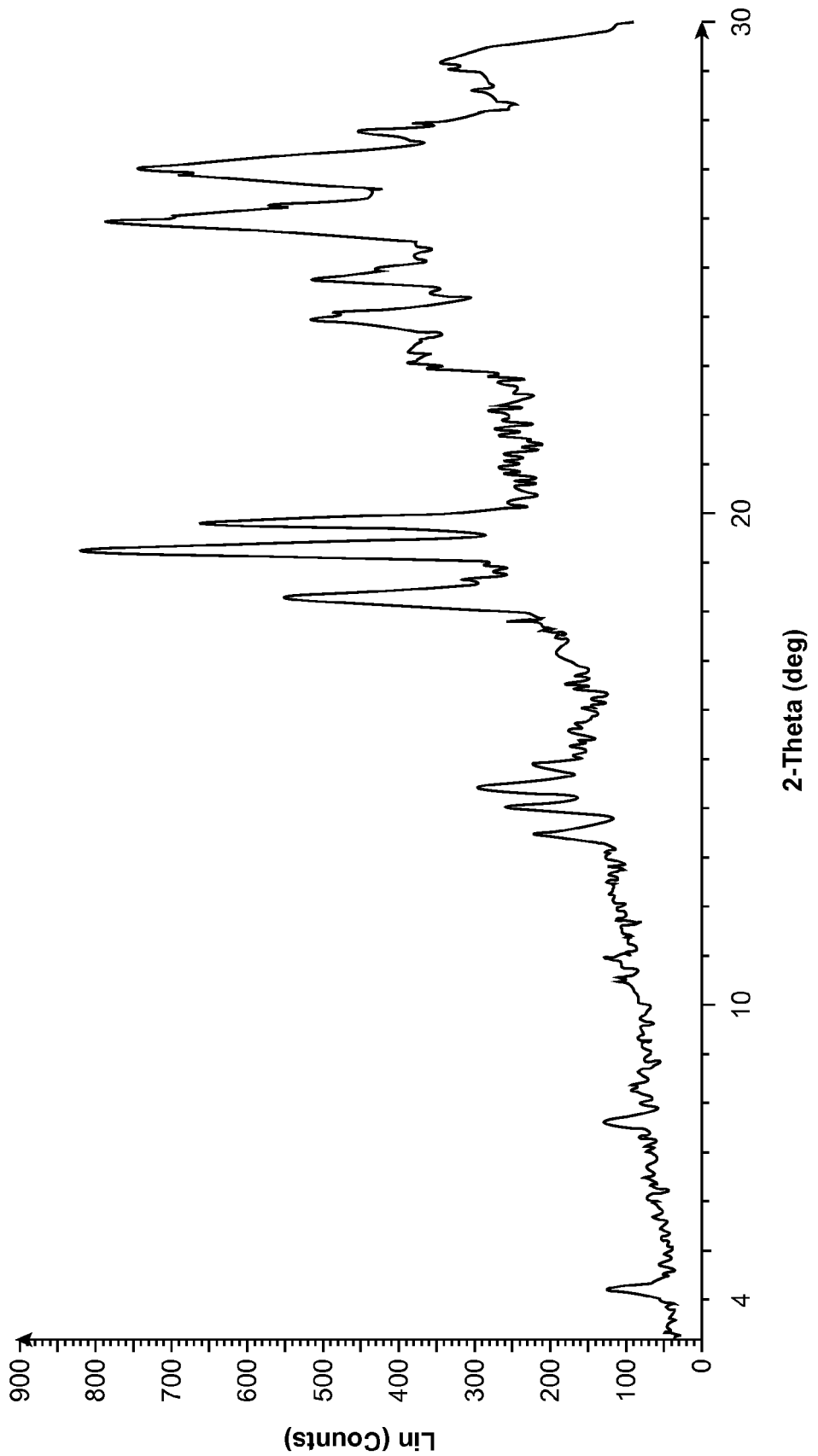
FIG. 16 provides an XRPD pattern of a crystalline form of the hydrochloride salt of Compound I.
Figure 29:
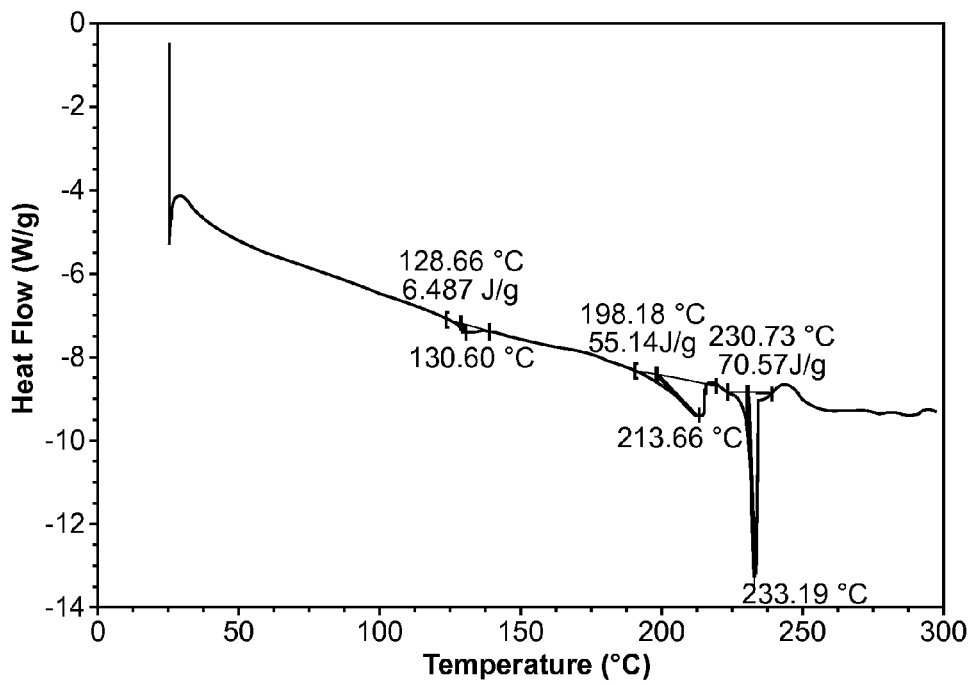
FIG. 29 provides a DSC analysis of a crystalline form of the hydrochloride salt of Compound I.
Figure 30:
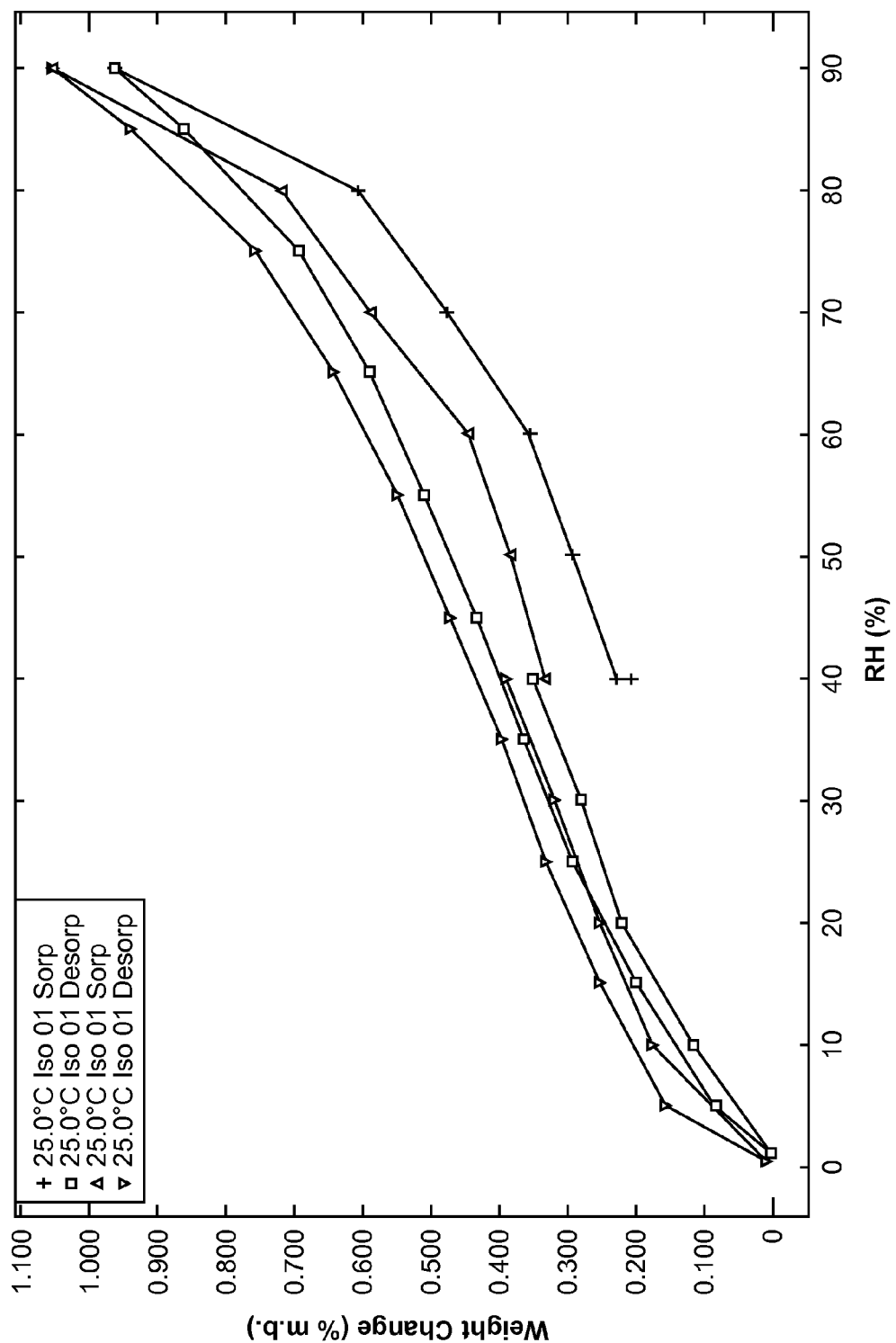
FIG. 30 provides a GVS analysis of a crystalline form of the hydrochloride salt of Compound I.

In another embodiment, this invention provides in a crystalline form of a hydrochloride salt of Compound I. In some embodiments, the crystalline form of the hydrochloride salt of Compound I shows an XRPD pattern which is substantially the same as the XRPD pattern of FIG. 16. In some embodiments, the crystalline form of Compound I hydrochloride salt shows a DSC and/or GVS analysis substantially the same as the DSC and GVS analysis represented by FIGS. 29 and 30, respectively.

In another aspect, at least a portion of the hydrochloride salt of Compound I is in the crystalline form. In some embodiments, about or greater than 50% by weight of the hydrochloride salt of Compound I is in the crystalline form. In some embodiments, about or greater than 60% by weight; about or greater than 65% by weight; about or greater than 70% by weight; about or greater than 75% by weight; about or greater than 80% by weight; about or greater than 85% by weight; about or greater than 90% by weight; about or greater than 95% by weight; or about or greater than 99% by weight of the hydrochloride salt of Compound I is in the crystalline form.

The identity of the salt forms of the present invention can also be confirmed by nuclear magnetic resonance (NMR), Fourier transform infrared (FTIR) and mass spectrometry (MS). Purity and water content can be determined by reverse phase high-performance liquid chromatography (HPLC) and Karl Fischer titration method, respectively. Residue solvent content can be determined by gas chromatography (GC). The following are certain analytical methods that can be employed to determine the identity, purity and properties of the salts or crystalline forms of this invention. Exemplary procedures for these analytical methods are described in Example 10 below.

Proton NMR,
FTIR,
Mass Spectroscopy,
HPLC for mesylate content,
Purity was determined based on related substances,
Karl Fischer for water content,
Trace metals and silicon analyses (inductively coupled plasma (ICP) Method),
Elemental analysis by combustion for carbon, hydrogen, nitrogen, by colorimetric titration for sulfur, and by ion chromatography for chlorine,
GC for residual solvents.

A number of methods are useful for the preparation of the salts described above and are known to those skilled in the art. For example, reaction of Compound I with one or more molar equivalents of the desired acid, such as hydrochloric acid, maleic acid, thiocyanic acid, 1-hydroxy-2-naphthoic acid, methanesulfonic acid, or phosphoric acid, in a solvent or solvent mixture in which the salt is insoluble, or in a solvent like water after which the solvent is removed by evaporation, distillation or freeze drying. Alternatively, Compound I may be passed over an ion exchange resin to form the desired salt or one salt form of the product may be converted to another using the same general process. The crystalline forms provided herein may be obtained by direct crystallization of the salt of Compound I or by crystallization of the salt of Compound I followed by interconversion from another crystalline form or from an amorphous state. Exemplifying procedures are provided in the Examples.

Therapeutic Methods

The salts of Compound I or crystalline forms of a salt of Compound I can be used for preventing or treating a condition in a mammal characterized by undesired thrombosis. In some embodiments, a therapeutically effective amount the salt or a crystalline form of the salt of Compound I is administered to the mammal in need of such treatment. The salt or a crystalline form of the salt of Compound I can be used either alone or in conjunction with pharmaceutically acceptable excipients to prevent the onset of a condition characterized by undesired thrombosis. Prophylactic treatment can have substantial benefits for a patient at risk of an ailment, through decreased medical treatments and their associated mental and physical costs, as well as the direct monetary savings from avoiding prolonged treatment of a patient. For patients where the condition is not detected sufficiently early to prevent onset, the compounds or salts that can be prepared by the present invention, for example the salt of Compound I can be used either alone or in conjunction with pharmaceutically acceptable excipients to treat the condition.

Compound I is characterized by its ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The salts of Compound I or crystalline forms of a salt of Compound I of the present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

In some embodiments, the salts and crystalline forms of Compound I are useful in treating thrombosis and conditions associated with thrombosis. Accordingly, a method for preventing or treating a condition in a mammal characterized by undesired thrombosis comprises administering to the mammal a therapeutically effective amount of a salt or a crystalline form of the salt of Compound I of this invention. The salts and crystalline forms of Compound I are useful in treating undesired thrombosis and/or associated conditions including, but not limited to, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboanglitis obliterans, thrombotic disease associated with heparin-induced thrombocytopenia, thrombotic complications associated with extracorporeal circulation, thrombotic complications associated with instrumentation, thrombotic complications associated with the fitting of prosthetic devices, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

In some embodiments, the condition is selected from the group consisting of embolic stroke, thrombotic stroke, venous thrombosis, deep venous thrombosis, acute coronary syndrome, and myocardial infarction.

In some embodiments, the salts and crystalline forms of Compound I are useful in: prevention of stroke in atrial fibrillation patients; prevention of thrombosis in medically ill patients; prevention and treatment of deep vein thrombosis; prevention of arterial thrombosis in acute coronary syndrome patients; and/or secondary prevention of myocardial infarction, stroke or other thrombotic events in patients who have had a prior event.

The salts of Compound I or crystalline forms of a salt of Compound I of this invention can also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g.

when contacting the mammal's blood with material selected from the group consisting of vascular grafts, stents, orthopedic prosthesis, cardiac prosthesis, and extracorporeal circulation systems.

Besides being useful for human treatment, the salts or crystalline forms of a salt of Compound I are also useful for veterinary treatment of companion animals, exotic animals and farm animals, including mammals, rodents, and the like. More preferred animals include horses, dogs, and cats.

Pharmaceutical Compositions and Administration

The pharmaceutical compositions comprising the salts of Compound I or crystalline forms of a salt of Compound I described herein can be used for preventing or treating a subject suffering from a disease condition, wherein the disease condition is characterized by undesired thrombosis. In some embodiments, the pharmaceutical compositions are comprised of a pharmaceutically acceptable carrier and a therapeutically effective amount of a mesylate, phosphate, 1-hydroxy-2-naphthoate or thiocynate salt of Compound I optionally in a crystalline polymorph form.

In the management of thrombotic disorders the salts of Compound I or crystalline forms of a salt of Compound I may be utilized in compositions such as tablets, capsules, lozenges or elixirs for oral administration, suppositories, sterile solutions or suspensions or injectable administration, and the like, or incorporated into shaped articles. Subjects in need of treatment (typically mammalian) using the salts of Compound I or crystalline forms of a salt of Compound I of this invention can be administered in dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these salts or crystalline forms are employed, and other factors which those skilled in the medical arts will recognize.

Typical adjuvants which may be incorporated into tablets, capsules, lozenges and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. Sterile compositions for injection can be formulated according to conventional pharmaceutical practice.

Capsules useful in the present invention can be prepared using conventional and known encapsulation techniques, such as that described in Stroud et al., U.S. Pat. No. 5,735, 105. The capsule is typically a hollow shell of generally cylindrical shape having a diameter and length sufficient so that the pharmaceutical compositions containing the appropriate dose of the active agent fit inside the capsule. The interior of the capsules can include plasticizer, gelatin, modified starches, gums, carrageenans and mixtures thereof Liquid carriers such as water, saline, or a fatty oil can also be present. Those skilled in the art will appreciate what compositions are suitable.

In addition to the active agent, tablets useful in the present invention can comprise fillers, binders, compression agents, lubricants, disintegrants, colorants, water, talc and other elements recognized by one of skill in the art. The tablets can be homogeneous with a single layer at the core, or have multiple layers in order to realize preferred release profiles. In some instances, the tablets of the instant invention may be coated, such as with an enteric coating. One of skill in the art will appreciate that other excipients are useful in the tablets of the present invention.

Lozenges useful in the present invention include an appropriate amount of the active agent as well as any fillers, binders, disintegrants, solvents, solubilizing agents, sweeteners, coloring agents and any other ingredients that one of skill in the art would appreciate is necessary. Lozenges of the present invention are designed to dissolve and release the active agent on contact with the mouth of the patient. One of skill in the art will appreciate that other delivery methods are useful in the present invention.

Formulations of the salts of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the salts or crystalline forms of a salt of Compound I of this invention to be used for therapeutic administration may be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. Route of administration may be by injection, such as intravenously (bolus and/or infusion), subcutaneously, intramuscularly, colonically, rectally, nasally or intraperitoneally, or employing a variety of dosage forms such as suppositories, implanted pellets or small cylinders, aerosols, oral dosage formulations (such as tablets, capsules and lozenges) and topical formulations such as ointments, drops and dermal patches. The sterile of this invention are desirably incorporated into shaped articles such as implants which may employ inert materials such as biodegradable polymers or synthetic silicones, for example, Silastic, silicone rubber or other polymers commercially available.

The salts or crystalline forms of a salt of Compound I of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The salts or crystalline forms of a salt of Compound I of this invention may also be delivered by the use of antibodies, antibody fragments, growth factors, hormones, or other targeting moieties, to which the salt molecules are coupled. The salts or crystalline forms of a salt of Compound I of this invention may also be coupled with suitable polymers as targetable drug carriers. Such polymers can include polyvinylpyrrolidinone, pyran copolymer, polyhydroxy-propyl-methacrylamide-phenol, polyhydroxyethyl-aspartamide-phenol, or polyethyleneoxide-polylysine substituted with palmitoyl residues. Furthermore, salts or crystalline forms of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

In some embodiments, the pharmaceutical composition comprises a pharmaceutically acceptable carrier and the mesylate, phosphate, 1-hydroxy-2-naphthoate or thiocynate salt of Compound I or a crystalline form thereof, wherein the pharmaceutical composition is in a solid form or a suspension in a liquid excipient and the salt or a crystalline form of the salt of Compound I provides improved thermo and/or hydrolytic stability, handling, purity, which provides improved efficacy and/or safety profile.

In some embodiments, the pharmaceutical composition comprises a pharmaceutically acceptable carrier and is prepared from the salt or a crystalline form of the salt of Compound I, wherein the pharmaceutical composition is in a liquid solution form and the salt or a crystalline form of Compound I provides improved thermo and hydrolytic stability, handling, purity and solubility, which provides improved efficacy and/or safety profile. Liquid formulations of the salts and crystalline forms of Compound I can be prepared by, for example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Therapeutic compound liquid formulations generally are placed into a container having a sterile access port, for example, an intravenous solution bag or vial having a stopper pierceable by hypodermic injection needle.

Typically, about 0.5 to 500 mg of the salt or a crystalline form of the salt of Compound I is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

It is contemplated that a typical dosage of Compound I will range from about 0.001 mg/kg to about 1000 mg/kg, preferably from about 0.01 mg/kg to about 100 mg/kg, and more preferably from about 0.10 mg/kg to about 20 mg/kg. Advantageously, the salts or crystalline forms of this invention may be administered several times daily, and other dosage regimens may also be useful.

Therapeutically effective dosages may be determined by either in vitro or in vivo methods. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency may need to be individually determined for each salt or crystalline form by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of Compound I are commenced at lower dosage levels, with dosage levels being increased until the desired effect is achieved.

EXAMPLES

Unless stated otherwise, the abbreviations used throughout the specification have the following meanings:

| | |
|---|---|
| A% = | total percent area |
| mA = | milliampere |
| aq. = | aqueous |
| AUC = | area under curve |
| $CH_3SO_3H$ = | methanesulfonic acid |
| cm = | centimeter |
| CuI = | copper (I) iodide |
| d = | doublet |
| deg = | degree |
| DIPEA = | diisopropylethylamine |
| DMSO = | dimethyl sulfoxide |
| DSC = | differential scanning calorimetry |
| EDTA = | ethylenediaminetetraacetic acid |
| eq. or equiv = | equivalent |
| $Et_3SiH$ = | triethyl silane |
| EtOAc = | ethyl acetate |
| EtOH = | ethanol |
| g = | gram |
| $H_2SO_4$ = | sulfuric acid |
| HPLC = | high performance liquid chromatography |
| hr = | hour |
| Hz = | hertz |
| FTIR = | Fourier transform infrared |
| IC = | ion chromatography |
| ICP = | inductively coupled plasma |
| IPA = | Isopropanol |
| IR = | infrared |
| J = | coupling constant |
| $K_2CO_3$ = | potassium carbonate |
| kg = | kilogram |
| L = | liter |
| LOD = | limit of detection |
| M = | molar |
| m = | multiplet |
| Me = | methyl |
| MeCN = | acetonitrile |
| MEK = | methyl ethyl ketone |
| MeO = | methoxy |
| MeOH = | methanol |
| MeTHF = | methyltetrahydrofuran |
| mg = | milligram |
| min. = | minute |
| mL = | milliliter |
| mm = | millimeter |
| mmHg = | millimeters of mercury |
| MTBE = | methyl tert butyl ether |
| N = | normal |
| $Na_2SO_4$ = | sodium sulfate |
| $NH_3$ = | ammonia |
| nM = | nanomolar |
| NMR = | nuclear magnetic resonance |
| PhMe = | toluene |
| ppm = | parts per million |
| RH = | relative humidity |
| rpm = | revolutions per minute |
| r.t. = | room temperature |
| s = | singlet |
| TGA = | thermal gravimetric analysis |
| TDS = | total dissolved solids |
| TFA = | trifluoroacetic acid |
| THF = | tetrahydrofuran |
| Wt = | weight |
| μM = | micromolar |

U.S. Provisional Patent Application No. 61/287,679, filed Dec. 17, 2009, and U.S. patent application Ser. No. 12/970,531, filed on Dec. 16, 2010, both titled "Methods Of Preparing Factor Xa Inhibitors And Salts Thereof," and U.S. Pat. No. 7,763,608, describe processes of preparing Compound I, all of which are incorporated by reference in their entirety.

Example 1

Preparation of Compound C

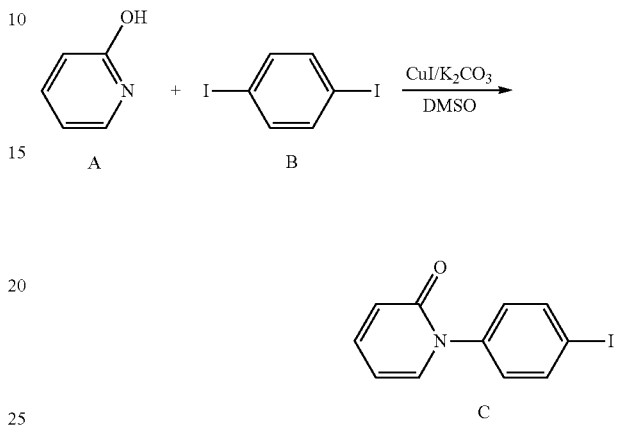

121.1 kg of 1,4-diiodobenzene B (0.367 mol) was charged as a solid to a 200-gallon reactor containing DMSO followed by 35 kg of 2-hydroxypyridine A (0.368 mol), 123 kg of $K_2CO_3$ (4.8 equiv), and 7.3 kg CuI (0.1 equiv). The mixture was heated to 120±5° C. for 3 hours. The reaction monitored by HPLC for completion. The reaction after cooling was quenched with water and ethyl acetate (EtOAc). The organic layer was washed with brine followed by $Na_2SO_4$ drying. After filtration, the EtOAc layer was concentrated at 85° C. followed by addition of heptanes. The slurry was then cooled to 20° C. for 1 hour and isolated via a cleaned and dried centrifuge. The product was collected and dried for 16 hours at 35° C. under about 28 mmHg. Recovery was 55.1 kg (50% yield) of Compound C, with 85.9% AUC purity.

Example 2

Preparation of Compound E

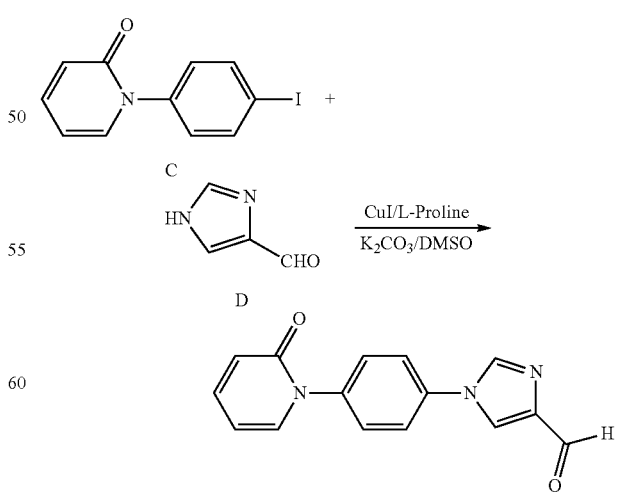

CuI (2.95 kg, 0.20 equiv) and L-proline (1.88 kg, 0.20 equiv) were mixed for 15 minutes in DMSO (253 kg). To this was added Compound C (24 kg, 1.0 equiv), $K_2CO_3$ (22.8 kg, 4.1 equiv), and 4-formylimidazole D (8.30 kg, 1.07 equiv). The reaction mixture was then heated to 120±5° C. for 3.5 hours. HPLC analysis concluded the reaction was complete and the mixture was cooled to 20±5° C. The reaction was diluted with water (40 volumes) and dichloromethane (DCM) (20 volumes), stirred for 1 hour, and centrifuged. In order to remove the insoluble impurities, the centrifuge filtrates were then polished filtered across a press fitted with 1-micron paper. The layers were separated, organic layer dried with $Na_2SO_4$, and filtered. The organic filtrates were atmospherically distilled to reduce the volume, charged with EtOAc, and continued to distill to an internal temperature of about 72° C. The product slurry was cooled to about 20° C. for 2 hours and isolated 6.5 kg of the aldehyde intermediate Compound E (30.4% yield).

Example 3

Preparation of Compound G

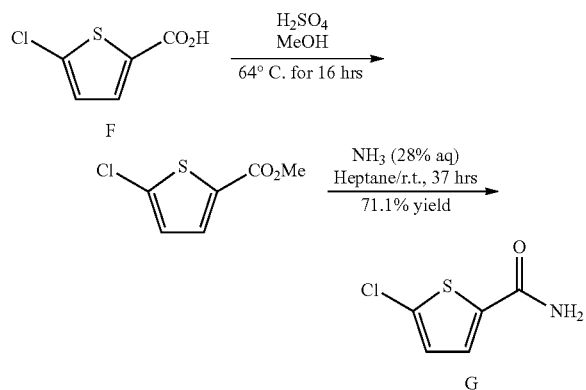

The 200-gallon reactor was charged with methanol (135 kg), 5-chlorothiophene-2-carboxylic acid F (12 kg, 73.81 mol, 1.0 equiv), and sulfuric acid (6.7 kg, 68.31 mol) under nitrogen. The contents were warmed to reflux (64° C.) for 16 hours and reaction completion monitored by HPLC. The reactor was cooled to 40° C. and the mixture was vacuum distilled to an oil at <50° C. The methyl ester obtained was cooled to 20° C. and ammonium hydroxide (157 kg, 2586 mol, 35.2 equiv) was charged along with heptane (10 kg) to the reactor. The reactor contents were mixed for 36 hours at ambient temperature. The completion of the reaction was monitored by HPLC for the disappearance of methyl ester intermediate. The precipitated solids were centrifuged and washed with water followed by heptane. The isolated solids were dried at 45° C. for 14 hours to afford Compound G (8.42 kg, 77.1% yield).

Example 4

Preparation of Compound I

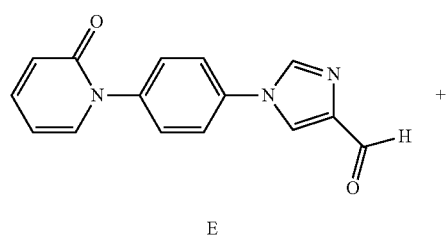

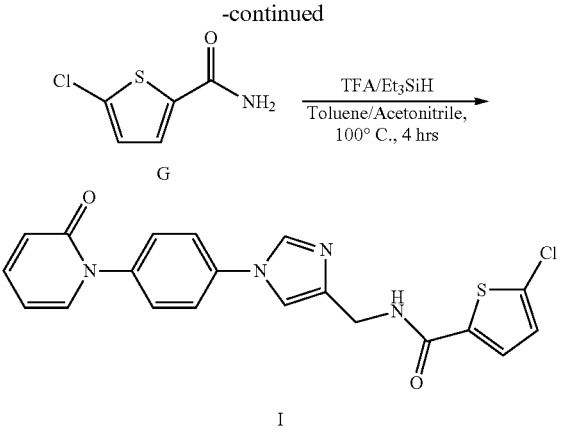

A nitrogen-inerted 200-gallon reactor was charged with toluene (202.4 kg), 1-(4-(2-oxopyridin-1(2H)-yl)phenyl)-1H-imidazole-4-carbaldehyde (Compound E, 11.7 kg, 1.0 equiv) and 2-amido-5-chlorothiophene (Compound G, 7.8 kg, 1.09 equiv). The contents were mixed together for 15 minutes followed by the addition of triethylsilane ($Et_3SiH$) (15.3 kg, 3.0 equiv) and trifluoroacetic acid (15.3 kg, 3.0 equiv). The reaction mixture was heated at 100±5° C. for 4 hours and the reaction monitored by HPLC analysis. The reaction was complete when Compound E was less than 1%. The reaction mixture was cooled to 40±5° C. and acetonitrile (139.2 kg) was added and reaction further cooled to 15±5° C. While maintaining the temperature at or below about 35° C., diisopropylethylamine (DIPEA) (18.7 kg, 3.3 equiv) was added over 15 minutes. The reaction contents were stirred for 1 hour at 20° C. and the solid Compound I isolated on a centrifuge. The collected free base of Compound I was vacuum dried at 45° C. and 28 mmHg for 32 hours. Compound I (10.89 kg, 60.2% yield) was collected as tan solid. HPLC record purity as area %: 93.5%. Structure was confirmed by Infrared (IR) spectrum.

Example 5

Primary Screen of Salts of Compound I

In a screen of salt formation of Compound I, five acids in five solvents were investigated. Due the low solubility of Compound I free base in a range of organic solvents, the salt formation was carried out as slurries. Compound I free base (20 mg, 48 μmol) was treated with the solvent (500 μL) and the acid as indicated in Table 1 (1.1 equivalents as a solution in solvent or as a solid) was then added and the reactions placed in a maturation chamber for sixteen hours. Detailed conditions and results are listed in Tables 2 and 3.

Based on XRPD results confirming crystalline solids, one solid form of the thiocyanate salt, three solid forms of the phosphate salt and one solid form of the 1-hydroxy-2-naphthoate salt were identified. As indicated below, glutamic acid and aspartic acid reactions consistently returned the free base under the reaction conditions. This is contemplated to be attributed to the low solubility of both the free base and the free acids. Ion chromatography and ICP analysis can be used to quantify the stoichiometry of inorganic anion present and further weigh that salts had been formed.

TABLE 1

Array of solvents and acids used in primary screen

| Exp | Acid | Solvent | Observation on addition of solvent | Observation on addition of acid |
| --- | --- | --- | --- | --- |
| 1-1 | Thiocyanic acid 1M in H₂O | IPA | Suspension | Suspension |
| 1-2 | L-Aspartic acid -solid | IPA | Suspension | Suspension |
| 1-3 | Phosphoric acid 1M in THF | IPA | Suspension | Suspension |
| 1-4 | L-Glutamic acid - solid | IPA | Suspension | Suspension |
| 1-5 | 1-Hydroxy-2-Naphthoic acid 1M in THF | IPA | Suspension | Suspension |
| 1-6 | Thiocyanic acid 1M in H₂O | 2-MeTHF | Suspension | Suspension |
| 1-7 | L-Aspartic acid -solid | 2-MeTHF | Suspension | Suspension |
| 1-8 | Phosphoric acid 1M in THF | 2-MeTHF | Suspension | Suspension |
| 1-9 | L-Glutamic acid - solid | 2-MeTHF | Suspension | Suspension |
| 1-10 | 1-Hydroxy-2-Naphthoic acid 1M in THF | 2-MeTHF | Suspension | Suspension |
| 1-11 | Thiocyanic acid 1M in H₂O | PhMe | Suspension | Suspension |
| 1-12 | L-Aspartic acid -solid | PhMe | Suspension | Suspension |
| 1-13 | Phosphoric acid 1M in THF | PhMe | Suspension | Suspension |
| 1-14 | L-Glutamic acid - solid | PhMe | Suspension | Suspension |
| 1-15 | 1-Hydroxy-2-Naphthoic acid 1M in THF | PhMe | Suspension | Suspension |
| 1-16 | Thiocyanic acid 1M in H₂O | MEK | Suspension | Suspension |
| 1-17 | L-Aspartic acid -solid | MEK | Suspension | Suspension |
| 1-18 | Phosphoric acid 1M in THF | MEK | Suspension | Suspension |
| 1-19 | L-Glutamic acid - solid | MEK | Suspension | Suspension |
| 1-20 | 1-Hydroxy-2-Naphthoic acid 1M in THF | MEK | Suspension | Suspension |
| 1-21 | Thiocyanic acid 1M in H₂O | MeCN | Suspension | Suspension |
| 1-22 | L-Aspartic acid -solid | MeCN | Suspension | Suspension |
| 1-23 | Phosphoric acid 1M in THF | MeCN | Suspension | Suspension |
| 1-24 | L-Glutamic acid - solid | MeCN | Suspension | Suspension |
| 1-25 | 1-Hydroxy-2-Naphthoic acid 1M in THF | MeCN | Suspension | Suspension |

TABLE 2

Summary of results from primary salt screen.

| Exp. | Salt attempted | XRPD Result | ¹H NMR Result |
| --- | --- | --- | --- |
| 1-1 | Thiocyanate | Not free base - Form 1 | No shift observed |
| 1-2 | Aspartate | Not free base or acid | No shift observed, no acid seen |
| 1-3 | Phosphate | Not free base - Form 1 | No shift observed |
| 1-4 | Glutamate | Free base | n/a |
| 1-5 | 1-Hydroxy-2-naphthoate | Free base | n/a |
| 1-6 | Thiocyanate | Not free base- Form 1 | n/a |
| 1-7 | Aspartate | Similar to free base | n/a |
| 1-8 | Phosphate | Weak XRPD - Form 2 | No shift observed |
| 1-9 | Glutamate | Free base | n/a |
| 1-10 | 1-Hydroxy-2-naphthoate | Free base | n/a |
| 1-11 | Thiocyanate | Not free base- Form 1 | n/a |
| 1-12 | Aspartate | Similar to free base | n/a |
| 1-13 | Phosphate | Similar to free base | n/a |
| 1-14 | Glutamate | Similar to free base | n/a |
| 1-15 | 1-Hydroxy-2-naphthoate | Weak XRPD | n/a |
| 1-16 | Thiocyanate | Not free base- Form 1 | n/a |
| 1-17 | Aspartate | Similar to free base | n/a |
| 1-18 | Phosphate | Weak XRPD - Form 2 | No shift observed |
| 1-19 | Glutamate | Similar to free base + extra peaks | No shift observed, no acid seen |
| 1-20 | 1-Hydroxy-2-naphthoate | Free base | No shift observed, trace of acid seen |
| 1-21 | Thiocyanate | Not free base- Form 1 | n/a |
| 1-22 | Aspartate | Similar to free base + extra peaks | No shift observed, no acid seen |
| 1-23 | Phosphate | Not free base - Form 3 | No shift observed |
| 1-24 | Glutamate | Free base | n/a |
| 1-25 | 1-Hydroxy-2-naphthoate | Not free base - Form 1 | No shift observed 1eq acid seen |

Another salt screen experiment was done according to Table 3.

TABLE 3

| Acid | Solvent | Stoichiometry |
| --- | --- | --- |
| HCl | THF | 1:1 |
| HCl | MEK | 1:1 |
| HCl | EtOAc | 1:1 |
| HCl | $CH_3CN$ | 1:1 |
| maleic acid | MEK | 1:1 |
| maleic acid | $CH_3CN$ | 1:1 |
| Methanesulfonic acid | toluene | 1:1 |
| Methanesulfonic acid | MEK | 1:1 |
| Methanesulfonic acid | EtOAc | 1:1 |
| Methanesulfonic acid | dioxane | 1:1 |

Example 6

Maturation Experiments of Formation Salts of Compound I

The formation of selected salts of Compound I were repeated in 100-mg scales as indicated in Table 4. Formation of the thiocyanate salt did not repeat. The thiocyanate salt formation Experiment 2-1 produced a different result to the primary screen described above. A small amount of residue was obtained which was determined to be neither the free base nor the crystalline form previously identified. The liquor was evaporated to leave a gum like paste that did not crystallise during the course of the project. In the maturation experiments, Form 1 the phosphate salt could not be reproduced. Form 3 of the phosphate salt was obtained in two of the experiments. Form 1 of the 1-hydroxy-2-naphthoate salt is reproducible on 100-mg scale. The results are summarized in Table 5.

TABLE 4

Acids and solvents used in 100-mg maturation experiments.

| Exp. | Acid | Solvent |
| --- | --- | --- |
| 2-1 | Thiocyanic acid | MeCN |
| 2-2 | Phosphoric acid | IPA |
| 2-3 | Phosphoric acid | MEK |
| 2-4 | Phosphoric acid | MeCN |
| 2-5 | 1-hydroxy-2-naphthoic acid | MeCN |

To assess the stability of the salts to elevated temperature and humidity, samples of the phosphate and 1-hydroxy-2-naphthoate salts were stored at 40° C./75% RH for a total of seventeen days at which point they were analyzed by XRPD. Their chemical purity was also assessed by HPLC and is shown in Table 6. No significant thermal events were seen before degradation began for both the phosphate salt and the 1-hydroxy-2-naphthoate salts.

TABLE 6

HPLC Purity Pre and Post 40° C./75% RH

| Material | Purity as isolated | Purity post 40° C./75% RH |
| --- | --- | --- |
| Phosphate 2-4 | 98.0% | 97.3% |
| 1-Hydroxy-2-naphthoate 2-5 | 98.2% | 97.7% |

GVS was carried out on both the phosphate salt Form 2, and on the 1-hydroxy-2-naphthoate salt Form 1. Neither salts showed hygroscopicity and only the 1-hydroxy-2-naphthoate salt Form 1 showed any hysteresis.

The 40° C./75% RH study on the phosphate salt Form 2 showed that the material is stable to these conditions with respect to solid form and chemical purity. The 1-hydroxy-2-naphthoate salt is also stable under these conditions. There was a loss of crystallinity in the phosphate Form 3 upon storage at 40° C./75% RH and a drop of 0.7% in its chemical purity, but no change in its solid form. The 1-hydroxy-2-naphthoate salt also shows a loss of crystallinity and a drop of 0.5% in it chemical purity, but no change in its solid form.

Salt formation attempts of Compound I with five pharmaceutically acceptable counter ions lead to the reproducible formation of mono phosphate and mono 1-hydroxy-2-naphthoate salts.

Three solid forms of the phosphate salt were identified in these experiments. Form 1 was not reproduced. Forms 2 and 3 were concluded to be anhydrous by thermal and $^1$H NMR analysis.

Alternatively salt formations were carried out under reflux conditions. Compound I (300 mg) was treated with solvent (13 mL) and brought to a gentle reflux. Acid (1.1 eq) was added and the reactions refluxed for ten minutes. The heating was turned off and the reactions were cooled to ambient with stirring. The results are summarized in Table 7.

TABLE 5

Summary of Analytical Data from 100-mg Maturation Experiments

| Exp. | Salt attempted | XRPD data | $^1$H NMR | ICP analysis | IC analysis | HPLC Purity | Aqueous solubility |
| --- | --- | --- | --- | --- | --- | --- | --- |
| 2-1 | Thiocyanate | Not free base nor Form 1 | Insufficient material | Insufficient material | Insufficient material | Insufficient material | Insufficient material |
| 2-2 | Phosphate | Similar to free base | n/a | n/a | n/a | n/a | n/a |
| 2-3 | Phosphate | Form 3 | Not determined | Not determined | 1.07 eq phosphate | Not determined | Not determined |
| 2-4 | Phosphate | Form 3 | 0.04 eq MeCN | 6.89 and 6.90 | 1.02 eq phosphate | 98.0 | 6.9 mg · mL$^{-1}$ pH = 2.18 |
| 2-5 | 1-Hydroxy-2-naphthoate | Form 1 | No solvent, 1 eq acid | n/a | n a | 98.2 | 0.068 mg · mL$^{-1}$ pH = 6.50 |

TABLE 7

| Acid + Solvent | Yield | XRPD Result | $^1$H NMR | ICP Analysis | IC Analysis | HPLC Purity | Aqueous solubility |
|---|---|---|---|---|---|---|---|
| Phosphoric acid MEK | 384 mg | Partially crystalline, form 2 | No solvent | 6.62 and 6.65% P | 0.80 eq PO$_4$ | Not determined | Not determined |
| Phosphoric acid MeCN | 349 mg | Partially crystalline, form 2 | 0.04 eq MeCN | 7.41 and 7.52% P | 0.99 eq PO$_4$ | 98.0% | 4.1 mg/mL pH = 2.00 |
| 1-hydroxy-2-napthoic acid MeCN | 409 mg | Very similar to form 1 | No solvent, 1 eq acid | n/a | n/a | 98.1% | 0.044 mg/mL pH = 5.99 |

The thermal behaviour of the salts is consistent for the forms analysed from both the maturation and reflux methods. Losses observed in the TGA before decomposition are very small and events in the DSC occur after decomposition has started.

Example 7

Solubility Data of Selected Salts of Compound I

The aqueous thermodynamic solubility of selected salt forms was measured using the filtration method as described in Example 10. The results are detailed in Table 8.

phosphate salt. The 1-hydroxy-2-naphthoate salt, which only exhibited one solid form shows a much lower aqueous solubility than the mesylate salt Form A which is to be expected for this counter ion. The phosphate salt Forms 2 and 3 and the 1-hydroxy-2-naphthoate salt Form 1 are stable to elevated humidity and temperature with respect to solid form and chemical purity.

Example 8

Preparation of Methanesulfonate (Mesylate) Salt of Compound I

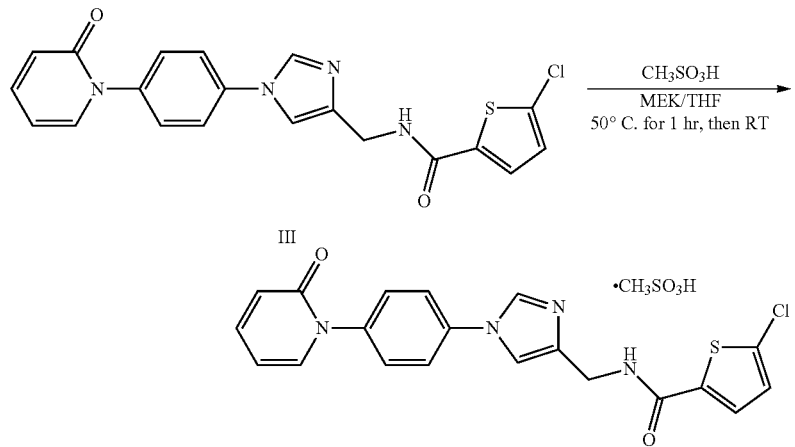

TABLE 8

| Salt and Form | Aqueous solubility (mg · mL$^{-1}$) | pH |
|---|---|---|
| Mesylate Form A | 5.1 | 1.8 |
| Phosphate Form 2 | 4.1 | 2.0 |
| Phosphate Form 3 | 6.9 | 2.2 |
| 1-Hydroxy-2-naphthoate Form 1 | 0.05 | 6.0 |
| Hydrochloride salt | 0.4 | 2.4 |
| Maleate salt | 0.3 | 2.7 |
| Free base | 0.0008 | 7.8 |

It was observed that the mesylate salt showed the greatest improvement in solubility at 5.1 mg/mL at pH 1.8. GVS data showed an uptake of 2.8 wt % at 90% RH with no hysteresis evident for the mesylate salt. The mono chloride and maleate which showed lower uptakes of 1.1 and 0.45 wt %, respectively. Both solid forms of the phosphate salt have comparable aqueous solubility with the mesylate salt Form A. However, there is evidence of propensity for polymorphism for the A slurry of free base of Compound I (10.89 kg, 1.0 equiv) in methylethyl ketone (MEK, 217 kg) was mixed for 30 minutes. To this slurry a THF solution (27.2 kg, 2.8 volumes) of methanesulfonic acid (MeSO$_3$H) (2.72 kg, 1.07 equiv) was added and the mixture heated at 50° C. for 1 hour. The mixture was cooled to 20° C. and stirred for 30 minutes. The mesylate salt was centrifuged and washed with MEK (32.7 kg). The product was dried at 45° C. under 28 mmHg vacuum for 116 hours and further dried at 61° C. for 60 hours. After drying, 12.50 kg the mesylate salt of Compound I (95.0% yield) was isolated in crystalline Form A.

Example 9

Preparation of Methanesulfonate (Mesylate) Salt of Compound I

The mesylate salt of Compound I 2.70 kg was charged to a glass-lined reactor, followed by acetone (39.70 kg), and USP water (4.35 kg). The solution was refluxed at 58° C. for approximately 1 hour followed by hot polish filtration through 0.2-micron cartridge filter. The polished filtrate was cooled to 20±5° C. followed by addition of methylethylketone (MEK) (32.80 kg) and stirred for 12 hours at ambient temperature. The slurry was cooled to 0-5° C. for more than 2 hours and then filtered through a filtration funnel. The solid isolated was dried at 50±5° C. under vacuum for at least 16 hours to afford the mesylate salt of Compound I (1.7 kg) as a tan crystalline Form B.

Example 10

Analysis of the Mesylate Salt of Compound I

To establish the structure of the mesylate salt of Compound I, the series of analyses listed below were performed. The identity was confirmed by NMR, Fourier transform infrared (FTIR) and mass spectrometry.
Proton NMR,
FTIR spectroscopy,
mass spectroscopy (MS),
HPLC for mesylate content,
Purity was determined based on related substances (HPLC), and
Elemental analysis by combustion for carbon, hydrogen, nitrogen, by colorimetric titration for sulfur, and by ion chromatography for chlorine.

X-Ray Powder Diffraction (XRPD)

X-Ray Powder Diffraction patterns were collected on a Bruker AXS C2 GADDS diffractometer by Bruker AXS Inc., Madison, Wis., USA using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm.

The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds.

The XRPD patterns for crystalline forms A and B of the mesylate salt of Compound I are shown in FIGS. 3, 4, 6 and 7, and Tables 9 and 10.

TABLE 9

Mesylate Form A XRPD Peak (2θ°) and % Intensity

| Angle (°2-Theta) | Intensity % |
|---|---|
| 6.05 | 5 |
| 12.05 | 10 |
| 13.45 | 5 |
| 14.85 | 25 |
| 17.0 | 25 |
| 17.35 | 25 |
| 18.05 | 50 |
| 18.75 | 15 |
| 19.20 | 15 |
| 19.75 | 15 |
| 20.30 | 100 |
| 20.95 | 35 |
| 21.85 | 35 |
| 23.20 | 80 |
| 24.5 | 10 |
| 25.05 | 15 |
| 26.13 | 50 |
| 26.85 | 60 |

TABLE 9-continued

Mesylate Form A XRPD Peak (2θ°) and % Intensity

| Angle (°2-Theta) | Intensity % |
|---|---|
| 29.55 | 10 |
| 30.31 | 15 |
| 31.75 | 20 |

TABLE 10

Mesylate Form B XRPD Peak (2θ°) and % Intensity.

| Angle (°2-Theta) | Intensity % |
|---|---|
| 12.35 | 18 |
| 13.97 | 20 |
| 15.52 | 20 |
| 15.55 | 20 |
| 16.96 | 42 |
| 18.55 | 25 |
| 18.95 | 40 |
| 20.41 | 35 |
| 21.30 | 35 |
| 21.85 | 52 |
| 22.75 | 50 |
| 23.45 | 20 |
| 24.35 | 20 |
| 25.65 | 30 |
| 25.75 | 40 |
| 26.65 | 65 |
| 27.4 | 20 |

The XRPD of crystalline forms of the phosphate salt, thiocyanate salt and 1-hydroxy-naphthoate salt of Compound I are shown in FIGS. 14, and 16-19. Table 11 shows the most intensive peaks of the crystalline forms for the phosphate salt, 1-hyrdoxy-2-naphthoate and thiocyanate of Compound I.

TABLE 11

| Salt | Form | | | | |
|---|---|---|---|---|---|
| | Phosphate Form 1 | Phosphate Form 2 | Phosphate Form 3 | 1-hyrdoxy-2-naphthoate Form 1 | thiocyanate Form 1 |
| Angle °2-theta | 5.4 | 6.5 | 4 | 4.3 | 5.02 |
| | 6.5 | 8.01 | 6.5 | 6 | 10.5 |
| | 9.5 | 8.78 | 8.2 | 8.45 | 11.8 |
| | 14.7 | 11.03 | 13.9 | 9 | 13.5 |
| | 15.6 | 14.5 | 14.5 | 10.5 | 14.01 |
| | 16.8 | 17.3 | 16 | 12.5 | 17.45 |
| | 17.9 | 18.2 | 17.45 | 15.01 | 18.3 |
| | 19.2 | | 18.23 | 15.7 | 21.95 |
| | 22.2 | | 19.15 | 17.4 | 23.02 |
| | 22.78 | | 20.12 | 18.45 | 24.5 |
| | 23.65 | | 21.45 | 24.3 | 25.01 |
| | | | 22.35 | 25.05 | 26.21 |
| | | | 23.5 | | 28.5 |
| | | | 24.02 | | 29.01 |
| | | | 25.2 | | |
| | | | 27.65 | | |
| | | | 28.25 | | |

Differential Scanning calorimetry (DSC)

DSC data were collected on a Mettler DSC 823e by Mettler-Toledo Inc., Columbus, Ohio, USA equipped with a 50 position auto-sampler. The instrument was calibrated for energy and temperature using certified indium. Typically 0.5-3 mg of each sample, in a pin-holed aluminum pan, was heated at 10° C./min from 25° C. to 350° C. A nitrogen purge at 50 mL/min was maintained over the sample. The differential scanning calorimetry (DSC) scans of Form A and Form B are provided in FIGS. 5, 8a, and 8b, respectively. The instrument control software was TA Instruments Q1000 and data analysis Universal Analysis 2000 v 4.3A Build 4.3.0.6.

Physicochemical Characterization

The physical chemical properties of Forms A and B were determined according to the procedures below and the data are summarized in Table 12.

Thermodynamic Aqueous Solubility By HPLC (Filtration Method)

Aqueous solubility was determined by suspending sufficient compound in water to give a maximum final concentration of $\geq 10$ mg/mL of the parent free-form of the compound. The suspension was equilibrated at 25° C. for 24 hours then the pH was measured. The suspension was then filtered through a glass fiber C filter into a 96 well plate. The filtrate was then diluted by a factor of 101. Quantitation was by HPLC with reference to a standard solution of approximately 0.1 mg/mL in DMSO. Different volumes of the standard, diluted and undiluted sample solutions were injected. The solubility was calculated using the peak areas determined by integration of the peak found at the same retention time as the principal peak in the standard injection.

Thermodynamic Aqueous Solubility By HPLC (Ultracentrifugation Method)

Aqueous solubility was determined by suspending sufficient compound in water to give a maximum final concentration of $\geq 10$ mg/mL of the parent free-form of the compound. The mixture was allowed to equilibrate for at least 48 hours at 37° C. under mild agitation. At each 24-48 hour interval, an aliquot was removed and the solution was separated from the solid via ultracentrifugation at >60,000 rpm for 20 min and then analyzed by HPLC for the concentration of the compound in the supernatant. Upon equilibration (concentration plateau is reached), the concentration was reported as solubility. This method is the preferred method in determining solubility as it attains the equilibrium and is measurement of the thermodynamic solubility.

TABLE 12

Physical and Chemical Characteristics of Two Crystalline Forms of the Mesylate Salt of Compound I

| Crystalline Form | Form A | Form B |
|---|---|---|
| Physical Appearance | Light yellow to tan crystalline solid | Light yellow to tan crystalline solid |
| Melting Point | 209° C. | 99° C. |
| Aqueous Solubility (Ultracentrifugation Method) | 2.0 mg/mL in water | 8.5 mg/mL in water |
| | 1.3 mg/mL in simulated gastric fluid | 12 mg/mL in simulated gastric fluid |
| | 0.02 mg/mL in simulated intestinal fluid | 0.06 mg/mL in simulated intestinal fluid |
| pH of saturated solution | 3.3 | 2.7 |
| Organic solvent solubility | Freely soluble in DMSO; Soluble in DMF, methanol; Sparingly soluble in PEG300; Slightly soluble in ethanol, methylene chloride, acetonitrile, isopropanol; Very slightly soluble in Dioxane, THF, acetone; and Practically insoluble or Insoluble in ethyl acetate | Same as left |
| pKa | 4.46 | Not determined |
| Log P | 2.25 | Not determined |
| Log D (7.4) | 2.85 | Not determined |
| Hygroscopicity | Absorbs approximately 2.5% moisture by weight between 0 and 90% relative humidity gradually | Absorbs approximately 2.5% moisture by weight between 0 and 90% relative humidity gradually | pKa Determination and Prediction:

Data were collected on a Sirius GlpKa instrument by Sirius Analytical Ltd., UK with a D-PAS attachment. Measurements were made at 25° C. in aqueous solution by UV and in methanol water mixtures by potentiometry. The titration media was ionic-strength adjusted (ISA) with 0.15 M KCl (aq). The values found in the methanol water mixtures were corrected to 0% co-solvent via a Yasuda-Shedlovsky extrapolation. The data were refined using Refinement Pro software v1.0. Prediction of pKa values was made using ACD pKa prediction software v9.

Log P & LogD Determination

Data were collected by potentiometric titration on a Sirius GlpKa instrument using three ratios of octanol:ionic-strength adjusted (ISA) water to generate Log P, Log Pion, and Log D values. The data were refined using Refinement Pro software v1.0. Prediction of Log P values was made using ACD v9 and Syracuse KOWWIN™ v1.67 software by Syracuse Research Corp., Syracuse, N.Y., USA.

Gravimetric Vapour Sorption (GVS).

Sorption isotherms were obtained using a SMS HT-DVS moisture sorption analyser by Surface Measurement Systems Limited, Middlesex, UK, controlled by SMS Analysis Suite software. The sample temperature was maintained at 25° C. by the instrument controls. The humidity was controlled by mixing streams of dry and wet nitrogen, with a total flow rate of 400 mL/min. The relative humidity was measured by a calibrated optical dew point transmitter (dynamic range of 0.5-100% RH), located near the sample. The weight change, (mass relaxation) of the sample as a function of % RH was constantly monitored by the microbalance (accuracy±0.005 mg).

Typically 5-20 mg of sample was placed in a tared mesh stainless steel liner within a stainless steel pan under ambient conditions. The sample was loaded and unloaded at 40% RH and 25° C. (typical room conditions).

A moisture sorption isotherm was performed as outlined in Table 13 (2 scans giving 1 complete cycle). The standard isotherm was performed at 25° C. at 10% RH intervals over a 0.5-90% RH range.

TABLE 13

| Parameters | Values |
| --- | --- |
| Adsorption-Scan 1 | 40-90 |
| Desorption/Adsorption - Scan 2 | 85-Dry, Dry-40 |
| Intervals (% RH) | 10 |
| Number of Scans | 2 |
| Flow rate (ml · min$^{-1}$) | 400 |
| Temperature (° C.) | 25 |
| Stability (° C. · min$^{-1}$) | 0.2 |
| Sorption Time (hours) | 3 |

Figure 4:
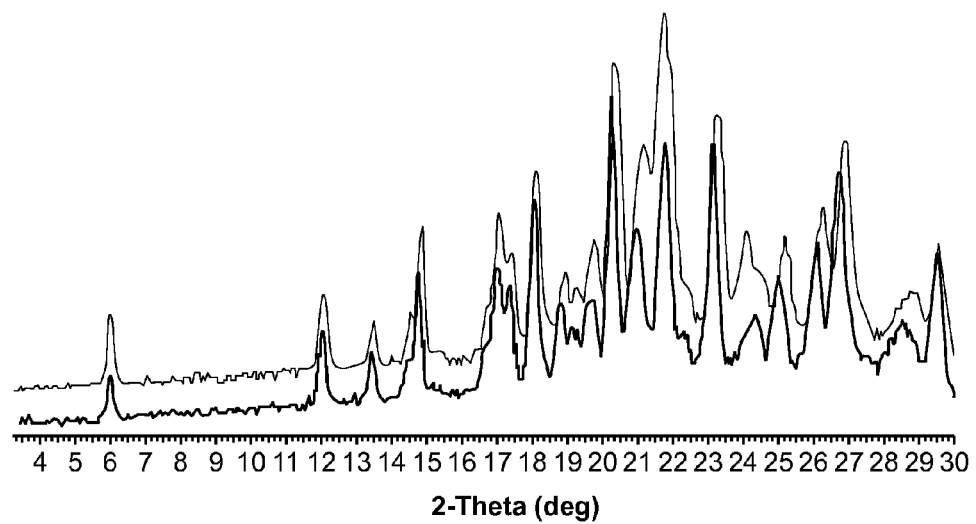
FIG. 4 provides an X-ray powder diffraction (XRPD) pattern of crystalline Form A of the mesylate salt of Compound I pre- and post-Gravimetric Vapour Sorption (GVS), in which Form A was exposed up to 90% RH at 25° C. and showed good physical stability after brief high moisture exposure.
Figure 7:
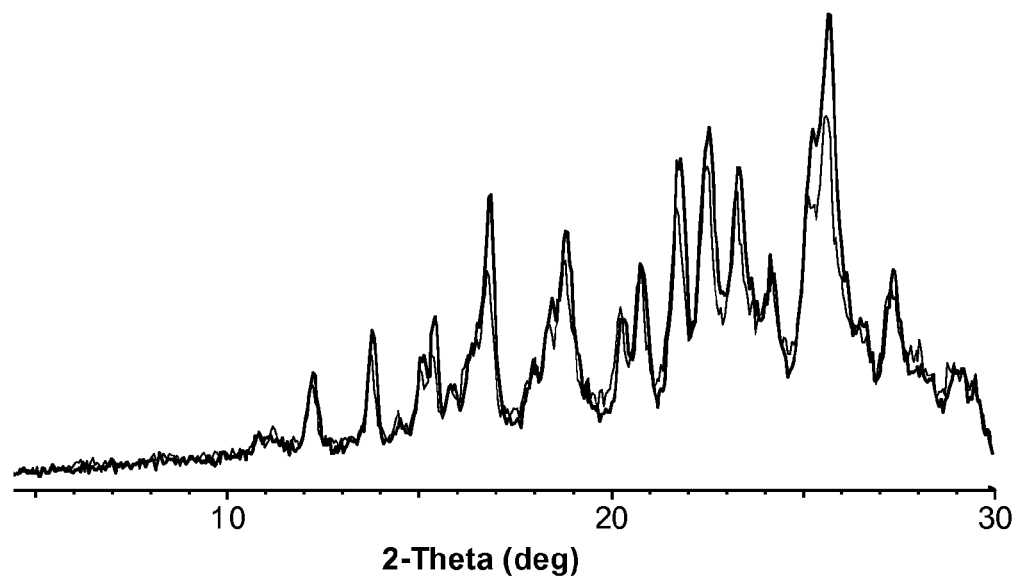
FIG. 7 provides an XRPD pattern of crystalline Form B of the mesylate salt of the compound of Formula I pre- and post-GVS (exposed up to 90% RH at 25° C.), which showed good physical stability of Form B after brief high moisture exposure.

The sample was recovered after completion of the isotherm and re-analysed by XRPD. The Compound I free base and mesylate Form A are physically stable after 6 month of storage at 40° C./75% RH. FIG. 4 shows the XRPD patterns of Compound I mesylate Form A pre- and post-DVS analysis (exposed up to 90% RH at 25° C.). FIG. 7 shows the XRPD patterns of Compound I mesylate Form B pre- and post-DVS analysis (exposed up to 90% RH at 25° C.). These figures indicate that both Form A and Form B have good physical stability after brief high moisture exposure.

Thermo-Gravimetric Analysis (TGA)

TGA data were collected on a Q500 TGA by TA Instruments, New Castle, Del., USA, equipped with a 16 position auto-sampler. The instrument was temperature calibrated using certified Alumel. Typically 5-30 mg of each sample was loaded onto a pre-tared platinum crucible and aluminium DSC pan, and was heated at 10° C.·min$^{-1}$ from ambient temperature to 350° C. A nitrogen purge at 60 ml·min$^{-1}$ was maintained over the sample.

The instrument control software was Thermal Advantage v4.6.6 and the data were analysed using Universal Analysis v4.3A.

Other methods known in the art can also be used to characterize the salts or crystalline forms of this invention.

Example 11

The following experiments were conducted using samples of Compound I prepared by a method disclosed in U.S. Pat. No. 7,763,608, which is incorporated by reference in its entirety.

Compound I was used in the rat investigation. An intravenous (IV) and oral (PO) dose of Compound I (1.0 and 10 mg/kg, respectively) was prepared. The IV dose was solubilized in 50% PEG300 to yield a final concentration of 1.0 mg/mL with a final pH of 5.13. The PO dose was suspended in 0.5% methylcellulose at a concentration of 2.0 mg/mL with a final pH of 2.70.

For the dog and monkey study, Compound I was also used. An IV and PO dose of Compound I (1.0 and 5.0 mg/kg, respectively) was prepared. The IV dose was formulated similarly to that used in the rat study (50% PEG300 in water). The PO dose was suspended in 0.5% methylcellulose at a concentration of 1.0 mg/mL with a final pH of approximately 3.50.

Study Design

A total of six male Sprague-Dawley rats (n=3/dosing group) from Charles River Laboratories (Hollister, Calif.), three male beagle dogs from Marshall BioResources (North Rose, N.Y.) and three male rhesus monkeys were utilized. All surgical procedures in rat (femoral and jugular vein catheterizations) were performed 8 days prior to utilization in the study and rats were acclimated in-house 5 days prior to utilization. Dogs were acclimated in-house at least seven days prior to utilization and were returned to the colony at the completion of the study. Monkey studies were conducted by an off-site contract laboratory.

All animals were fasted from the afternoon prior to study initiation to two hours post-dose (approximately 18 hours). Water was provided ad libitum. All animal rooms were on a 12 hour light-dark cycles (6 A.M. to 6 P.M.). On the morning of experimentation, animals were weighed. Rat femoral and jugular (IV only) vein blood lines were exteriorized and attached to access ports. Dogs were weighed and shaved at blood sampling and IV dosing sites (along both cephalic and saphenous veins).

All animals were dosed based on individual weights with a PO gavage volume of 5.0 mL/kg and an IV bolus dose volume of 1.0 mL/kg. Blood samples were obtained on 3.8% TSC (1:10 dilution) over a 24, 56, and 96 hour period post-dosing for the rat, dog, and monkey, respectively. Blood samples were centrifuged for platelet poor plasma, and resulting plasma was stored at −20° C. until sample analysis. Rat urine samples were collected on 200 μL of 2% boric acid from animals in the IV group at 0 (overnight), 10, and 24 hours post-dose. At collection times, urine volume and water consumption was recorded. Urine samples were stored at −20° C. until sample analysis.

Sample Analysis

Plasma and urine samples were analyzed for Compound I concentration using a liquid chromatography tandem mass spectrometry (LC/MS/MS). In brief, plasma and urine samples were processed in a 96-well Captiva™ filter plate (0.2 µm, Varian, Inc., Palo Alto, Calif.). Aliquots of plasma samples were precipitated with acetonitrile containing 500 ng/mL of N-(2-(5-chloropyridin-2-ylcarbaomoyl)-4-methoxyphenyl)-4-(N,N-dimethylcarbamimidoyl)-2-fluorobenzamide, an internal standard. Aliquots of urine samples were diluted with plasma before mixing with acetonitrile containing internal standard. The mixture was vortexed and refrigerated at 4° C. for 30 minutes to allow complete protein precipitation. The mixture was filtered into a 96-well collection plate. The filtrate was injected onto a Sciex API3000 LC/MS/MS equipped with a turbo-ion spray source. Compound I and N-(2-(5-chloropyridin-2-ylcarbaomoyl)-4-methoxyphenyl)-4-(N,N-dimethylcarbamimidoyl)-2-fluorobenzamide were separated on a Thermo Hypersil-Keystone Betasil $C_{18}$ column (4.6×100 mm, 5 µm; Fisher Scientific, Houston, Tex.). A mobile phase gradient mixture of 90% mobile phase A (0.5% formic acid in water) and 10% mobile phase B (0.5% formic acid in 90% acetonitrile) to 40% mobile phase B (programmed over 2.8 minutes). The peak areas of the m/z 411→250 product ion (Compound I) were measured against those of the m/z 470→342 product ion (N-(2-(5-chloropyridin-2-ylcarbaomoyl)-4-methoxyphenyl)-4-(N,N-dimethylcarbamimidoyl)-2-fluorobenzamide) in positive ion mode. The analytical range was 0.500 to 10,000 ng/mL.

Data Analysis

Sample Compound I concentrations below the lower limit of quantitation (LLQ) were reported as <0.500 ng/mL. These values were treated as zero for pharmacokinetic calculations.

Compound I pharmacokinetic parameter values were calculated by noncompartmental analysis of the plasma concentration-time data using Watson LIMS software (version 7.1). Terminal elimination rate constant (k) was calculated as the absolute value of the slope of linear regression of the natural logarithm (ln) of plasma concentration versus time during the terminal phase of the plasma concentration-time profile. Apparent terminal half-life ($T_{1/2}$) values were calculated as ln(2)/k. Area under the plasma concentration-time profile (AUC) values were estimated using the linear trapezoidal rule. $AUC_{all}$ values were calculated from time 0 to the time of the last detectable concentration. $AUC_{(0-inf)}$ values were calculated as the sum of the corresponding $AUC_{all}$ and the last detectable concentration divided by k. Systemic clearance (CL) was calculated from IV Dose/$AUC_{(0-inf)}$. Volume of distribution (Vz) was calculated from IV Dose/[k·$AUC_{(0-inf)}$]. Volume of distribution at steady-state (Vss) was calculated from CL* Mean Residence Time. Maximum plasma concentrations ($C_{max}$) and time to reach $C_{max}$ ($T_{max}$) were recorded as observed. Percentage oral bioavailability was calculated by taking the ratio of dose-normalized $AUC_{(0-inf)}$ values (AUC/D) following PO and IV administration. The results are shown in Tables 14 and 15.

TABLE 14

Pharmacokinetic parameters of Compound I in rat, dog, and monkey after intravenous administration determined by noncompartmental analysis

| Param- | | Mean ± SD | | |
|---|---|---|---|---|
| eter | Unit | Rat | Dog | Monkey |
| Dose | mg/kg | 1 | 1 | 1 |
| $T_{1/2}$ | hr | 2.86 ± 1.40 | | |
| $AUC_{all}$ | ng*hr/mL | 5376 ± 1186 | 1615 ± 360 | 12550 ± 5995 |
| $AUC_{(0-inf)}$ | ng*hr/mL | 5404 ± 1163 | 1622 ± 363 | 12560 ± 5998 |
| Vz | L/kg | 0.757 ± 0.328 | 2.73 ± 2.45 | 2.31 ± 1.71 |
| CL | mL/min/kg | 3.19 ± 0.734 | 10.7 ± 2.69 | 1.66 ± 1.06 |
| Vss | L/kg | 0.368 ± 0.026 | 0.843 ± 0.288 | 0.353 ± 0.059 |
| Dose excreted unchanged in urine | % | 0.248 ± 0.019 | | |

Noncompartmental analysis was performed using Watson LIMS software (version 7.1).
$T_{1/2}$: Terminal half-life
AUC: Area under the plasma concentration vs. time curve
Vz: Volume of distribution
CL: Systemic clearance
Vss: Volume of distribution at steady-state

TABLE 15

Pharmacokinetic parameters of Compound I in rat, dog, and monkey after oral administration determined by noncompartmental analysis

| Param- | | Mean ± SD | | |
|---|---|---|---|---|
| eter | Unit | Rat | Dog | Monkey |
| Dose | mg/kg | 10 | 5 | 5 |
| $T_{1/2}$ | hr | 2.72 ± 0.29 | | |
| $T_{max}$ | hr | 0.250 ± 0.00 | 0.583 ± 0.382 | 2.00 ± 0.00 |
| $C_{max}$ | ng/mL | 28890 ± 2084 | 2717 ± 474 | 6041 ± 1877 |
| $AUC_{all}$ | ng*hr/mL | 68510 ± 12510 | 5464 ± 1471 | 42140 ± 17240 |
| $AUC_{(0-inf)}$ | ng*hr/mL | 68590 ± 12490 | 5475 ± 1475 | 42150 ± 17250 |
| AUC/D | kg*hr/mL | 6859 ± 1249 | 1095 ± 295 | 8430 ± 3449 |
| F | % | 127 ± 23.1 | 68.5 ± 15.5 | 71.6 ± 18.1 |

Noncompartmental analysis was performed using Watson LIMS software (version 7.1).
$T_{1/2}$: Terminal half-life
$T_{max}$: Time to reach maximal plasma concentration
$C_{max}$: Maximal plasma concentration
AUC: Area under the plasma concentration vs. time curve
% F: Absolute bioavailability Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A crystalline form of the mesylate salt of 5-chloro-N-((1-(4-(2-oxopyridin-1(2H)-yl)phenyl)-1H-imidazol-4-yl)methyl)thiophene-2-carboxamide, which is characterized by an X-ray powder diffraction pattern having at least six 2θ° peaks selected from the group consisting of: about 18.05±0.2, about 20.30±0.2, about 20.95±0.2, about 21.85±0.2, about 23.20±0.2, about 26.13±0.2, and about 26.85±0.2.

2. The crystalline form of claim 1, which is characterized by an X-ray powder diffraction pattern substantially the X-ray powder diffraction pattern as FIG. 3a or 3b.

3. The crystalline form of claim 1, which is further characterized by a differential scanning calorimetry pattern substantially the differential scanning calorimetry pattern as FIG. 5, or by the GVS analysis substantially the GVS analysis represented by FIG. 28.

4. A crystalline form of the mesylate salt of 5-chloro-N-((1-(4-(2-oxopyridin-1(2H)-yl)phenyl)-1H-imidazol-4-yl)methyl)thiophene-2-carboxamide, which is characterized by an X-ray powder diffraction pattern having at least four of 2θ° peaks selected from about 14.85±0.2, about 17.0±0.2, about 17.35±0.2, about 18.05±0.2, about 20.3±0.2, about 20.95±0.2, about 21.85±0.2, about 23.2±0.2, about 26.13±0.2, about 26.85±0.2, and about 31.75±0.2.

5. A crystalline form of the mesylate salt of 5-chloro-N-((1-(4-(2-oxopyridin-1(2H)-yl)phenyl)-1H-imidazol-4-yl)methyl)thiophene-2-carboxamide, which is characterized by an X-ray powder diffraction pattern having at least six of 2θ° peaks selected from about 14.85±0.2, about 17.0±0.2, about 17.35±0.2, about 18.05±0.2, about 20.3±0.2, about 20.95±0.2, about 21.85±0.2, about 23.2±0.2, about 26.13±0.2, about 26.85±0.2, and about 31.75±0.2.

6. A crystalline form of the mesylate salt of 5-chloro-N-((1-(4-(2-oxopyridin-1(2H)-yl)phenyl)-1H-imidazol-4-yl)methyl)thiophene-2-carboxamide, which is characterized by an X-ray powder diffraction pattern having at least the following 2θ° peaks: about 17.0±0.2, about 18.05±0.2, about 20.3±0.2, about 20.95±0.2, about 21.85±0.2, about 23.2±0.2, about 26.13±0.2, about 26.85±0.2, and about 31.75±0.2.

7. A crystalline form of the mesylate salt of 5-chloro-N-((1-(4-(2-oxopyridin-1(2H)-yl)phenyl)-1H-imidazol-4-yl)methyl)thiophene-2-carboxamide, which is characterized by an X-ray powder diffraction pattern having at least the following 2θ° peaks: about 6.05±0.2, about 12.05±0.2, about 13.02±0.2, about 14.85±0.2, about 17.0±0.2, about 17.30±0.2, about 18.05±0.2, about 20.3±0.2, about 20.95±0.2, about 21.85±0.2, about 23.2±0.2, about 26.13±0.2, about 26.85±0.2, about 29.55±0.2, and about 31.75±0.2.

8. A method for preparing the crystalline form of any one of claims 1-3 and 4-7 comprising combining the free base of 5-chloro-N-((1-(4-(2-oxopyridin-1(2H)-yl)phenyl)-1H-imidazol-4-yl)methyl)thiophene-2-carboxamide with at least one equivalent of methanesulfonic acid in a solvent comprising methylethyl ketone, and optionally tetrahydrofuran.

* * * * *